United States Patent
Shah et al.

(10) Patent No.: US 11,454,630 B2
(45) Date of Patent: Sep. 27, 2022

(54) MATERIALS AND METHODS FOR ASSESSING CANCER RISK AND TREATING CANCER

(71) Applicant: The Johns Hopkins University, Baltimore, MD (US)

(72) Inventors: Ami A. Shah, Ellicott City, MD (US); Livia Casciola-Rosen, Pikesville, MD (US); Antony Rosen, Pikesville, MD (US); Takeru Igusa, Baltimore, MD (US); Marikki K. Laiho, Kauniainen (FI)

(73) Assignee: The Johns Hopkins University, Baltimore, MD (US)

( * ) Notice: Subject to any disclaimer, the term of this patent is extended or adjusted under 35 U.S.C. 154(b) by 319 days.

(21) Appl. No.: 16/640,954

(22) PCT Filed: Aug. 23, 2018

(86) PCT No.: PCT/US2018/047770
§ 371 (c)(1),
(2) Date: Feb. 21, 2020

(87) PCT Pub. No.: WO2019/040760
PCT Pub. Date: Feb. 28, 2019

(65) Prior Publication Data
US 2020/0209245 A1 Jul. 2, 2020

Related U.S. Application Data

(60) Provisional application No. 62/549,711, filed on Aug. 24, 2017.

(51) Int. Cl.
*A61K 39/00* (2006.01)
*G01N 33/574* (2006.01)
*G01N 33/564* (2006.01)

(52) U.S. Cl.
CPC ..... *G01N 33/57488* (2013.01); *G01N 33/564* (2013.01); *G01N 2800/24* (2013.01); *G01N 2800/7028* (2013.01)

(58) Field of Classification Search
CPC combination set(s) only.
See application file for complete search history.

(56) References Cited

U.S. PATENT DOCUMENTS

| 9,624,549 B2 | 4/2017 | Rogan |
| 2004/0009474 A1 | 1/2004 | Leach |

(Continued)

FOREIGN PATENT DOCUMENTS

WO  WO 2016/183183  11/2016

OTHER PUBLICATIONS

European Search Report in International Appln. No. PCT/2018/047770, dated Apr. 9, 2021, 9 pages.

(Continued)

*Primary Examiner* — Lei Yao
(74) *Attorney, Agent, or Firm* — Fish & Richardson P.C.

(57) ABSTRACT

This document relates to materials and methods for assessing and/or treating subjects (e.g., subjects having autoimmune diseases). For example, materials and methods for determining if a subject (e.g., a human having an autoimmune disease) has one or more antibodies that can be used to identify the subject as having a lower risk of cancer or as having a higher risk of cancer are provided. Materials and methods for treating a subject (e.g., a human) identified as having a higher cancer risk for cancer are also provided.

4 Claims, 8 Drawing Sheets

(56) References Cited

U.S. PATENT DOCUMENTS

| | | |
|---|---|---|
| 2015/0185226 A1 | 7/2015 | Lambert |
| 2016/0303209 A1 | 10/2016 | Darrah et al. |
| 2017/0081322 A1 | 3/2017 | Laiho et al. |

OTHER PUBLICATIONS

PCT International Search report and Written Opinion in International Appln. No. PCT/US2018/047770, dated Oct. 29, 2018, 11 pages.

Abu-Shakra, et al., Cancer in systemic sclerosis. Arthritis and rheumatism 1993; 36(4): 460-4.

Airo, et al., Malignancies in Italian patients with systemic sclerosis positive for anti-RNA polymerase III antibodies. The Journal of rheumatology 2011; 38(7): 1329-34.

Bruni, et al., Resolution of paraneoplastic PM/Scl-positive systemic sclerosis after curative resection of a pancreatic tumour. Rheumatology 2017; 56(2): 317-8.

Chatterjee, et al., Risk of malignancy in scleroderma: a population-based cohort study. Arthritis and rheumatism 2005; 52(8): 2415-24.

Derk, et al., A cohort study of cancer incidence in systemic sclerosis. The Journal of rheumatology 2006; 33(6): 1113-6.

Hasegawa, et al., Systemic sclerosis revealing T-cell lymphoma. Dermatology, 1999; 198(1): 75-8.

Hill, et al., Risk of cancer in patients with scleroderma: a population based cohort study. Annals of the rheumatic diseases 2003; 62(8): 728-31.

Igusa et al. "Autoantibodies and Scleroderma Phenotype Define Subgroups at High-Risk and 1-58Low-Risk for Cancer," Annals of The Rheumatic Diseases, 2018, 77(8):1179-1118.

International Preliminary Report on Patentability in International Appln. No. PCT/US2018/047770, dated Feb. 25, 2020, 14 pages.

International Search Report in International Appln. No. PCT/US2018/047770, dated Oct. 29, 2018, 3 pages.

Joseph, et al., Association of the autoimmune disease scleroderma with an immunologic response to cancer. Science, 2014; 343(6167): 152-7.

Juarez, et al., Paraneoplastic scleroderma secondary to hairy cell leukaemia successfully treated with cladribine. Rheumatology 2008; 47(11): 1734-5.

Kang, et al., Incidence of cancer among patients with systemic sclerosis in Korea: results from a single centre. Scandinavian journal of rheumatology 2009; 38(4): 299-303.

Kuo, et al., Cancer risk among patients with systemic sclerosis: a nationwide population study in Taiwan. Scandinavian journal of rheumatology 2012; 41(1): 44-9.

Lazzaroni et al., Malignancies in Patients with Anti-RNA Polymerase III Antibodies and Systemic Sclerosis: Analysis of the EULAR Scleroderma Trials and Research Cohort and Possible Recommendations for Screening. The Journal of rheumatology 2017.

Leroy, et al., Scleroderma (systemic sclerosis): classification, subsets and pathogenesis. The Journal of rheumatology 1988; 15(2): 202-5.

Moinzadeh, et al., Association of anti-RNA polymerase III autoantibodies and cancer in scleroderma. Arthritis research & therapy 2014; 16(1): R53.

Nikpour, et al., Prevalence, correlates and clinical usefulness of antibodies to RNA polymerase III in systemic sclerosis: a cross-sectional analysis of data from an Australian cohort. Arthritis research & therapy 2011; 13(6): R211.

Olesen, et al., Systemic sclerosis and the risk of cancer: a nationwide population-based cohort study. The British journal of dermatology 2010; 163(4): 800-6.

Onishi, et al., Cancer incidence in systemic sclerosis: meta-analysis of population-based cohort studies. Arthritis and rheumatism 2013; 65(7): 1913-21.

Reimer et al. "Autoantibody to RNA polymerase I in Scleroderma Sera," The Journal of Clinical Investigation, 1987, 79(1):65-72.

Rosenthal, et al., Incidence of cancer among patients with svstemic sclerosis. Cancer 1995; 76(5): 910-4.

Rosenthal, et al., Scleroderma and malignancy: an epidemiological study. Annals of the rheumatic diseases 1993; 52(7): 531-3.

Sahai, et al., Confidence-Intervals for the Mean of a Poisson-Distribution—a Review. Biometrical J 1993; 35(7): 857-67.

Saigusa, et al., Association of anti-RNA polymerase III antibody and malignancy in Japanese patients with systemic sclerosis. J Dermatol 2015; 42(5): 524-7.

Shah et al. "Anti—RNPC-3 Antibodies as a Marker of Cancer-Associated Scleroderma," Arthritis & Rheumatology, 2017, 69(6):1306-1312.

Shah et al. "Close Temporal Relationship Between Onset of Cancer and Scleroderma in Patients With RNA Polymerase 1/111 Antibodies," Arthritis & Rheumatism, 2010, 62(9):2787-2795.

Shah et al., "Examination of Autoantibody Status and Clinical Features Associated With Cancer Risk and Cancer-Associated Scleroderma," Arthritis & Rheumatology, 2015, 67(4):1053-1061.

Shah, et al., Cancer and Scleroderma: A Paraneoplastic Disease with Implications for Malignancy Screening. Curr Opin Rheumatol. 2015;27(6):563-70.

Shah, et al., Review: cancer-induced autoimmunity in the rheumatic diseases. Arthritis & rheumatology 2015; 67(2): 317-26.

Siau, et al., Malignancy in scleroderma patients from south west England: a population-based cohort study. Rheumatology international 2011; 31(5): 641-5.

Subcommittee for scleroderma criteria of the American Rheumatism Association Diagnostic and Therapeutic Criteria Committee. Preliminary criteria for the classification of systemic sclerosis (scleroderma). Arthritis and rheumatism 1980; 23(5): 581-90.

Van Den Hoogen, et al., 2013 classification criteria for systemic sclerosis: an American College of Rheumatology/European League against Rheumatism collaborative initiative. Arthritis Rheum 2013; 65(11): 2737-47.

Xu et al. "Systematic Autoantigen Analysis Identifies a Distinct Subtype of Scleroderma with Coincident Cancer," Proc. Natl. Acad. Sci. U.S.A, 2016, 113(47):7526-7534.

MATERIALS AND METHODS FOR ASSESSING CANCER RISK AND TREATING CANCER

CROSS-REFERENCE TO RELATED APPLICATIONS

This application is a National Stage application under 35 U.S.C. § 371 of International Application No. PCT/US2018/047770 having an International Filing Date of Aug. 23, 2018, which claims the benefit of U.S. Patent Application Ser. No. 62/549,711, filed on Aug. 24, 2017. The disclosure of the prior applications are considered part of (and are incorporated by reference in) the disclosure of this application.

STATEMENT REGARDING FEDERAL FUNDING

This invention was made with government support under AR061439, AR053503, AR070254, CA172609, and CA193637 awarded by National Institutes of Health. The government has certain rights in the invention.

BACKGROUND

1. Technical Field

This document relates to materials and methods for assessing and/or treating subjects (e.g., subjects having autoimmune diseases). For example, this document provides materials and methods for determining if a subject (e.g., a human having an autoimmune disease) has one or more antibodies that can be used to identify the subject as having a lower risk of cancer or as having a higher risk of cancer. This document also provides materials and methods for treating a subject (e.g., a human) identified as having a higher risk for cancer.

2. Background Information

Subsets of patients with systemic sclerosis ("SSc," also referred to as "scleroderma") have an elevated risk of cancer compared to individuals in the general population (Onishi et al., 2013 *Arthritis & Rheumatism*, 65(7):1913-21; Shah et al., 2010 *Arthritis & Rheumatism*, 62(9):2787-95; and Shah et al., 2015 *Arthritis & Rheumatology*, 67(4):1053-61).

SUMMARY

This document relates to materials and methods for assessing and/or treating subjects (e.g., subjects having autoimmune diseases). For example, this document provides materials and methods for determining if a subject (e.g., a human having an autoimmune disease) has one or more antibodies described herein (e.g., anti-centromere antibodies, anti-POLR3 antibodies, anti-RPA194 antibodies, and/or anti-RNPC-3 antibodies) that can be used to identify the subject as having a lower risk of cancer or as having a higher risk of cancer. This document also provides materials and methods for treating a subject (e.g., a human) identified as having a higher cancer risk for cancer. For example, this document provides methods and materials for determining that a subject (e.g., a human having an autoimmune disease) is at a higher risk for cancer and administering one or more cancer treatments (e.g., one or more antibodies such as anti-centromere antibodies and/or anti-RPA194 antibodies) to treat the subject.

As demonstrated herein, autoantibody responses are associated with protection of scleroderma patients from cancer and the cancer risk of the human having scleroderma can be determined by detecting the presence or absence of one or more autoantibodies. For example, the presence of an anti-centromere antibody in a biological sample obtained from a subject having an autoimmune disease (e.g., scleroderma) can indicate that the subject has a lower risk for cancer. As another example, the presence of an anti-POLR3 antibody and an anti-RPA194 antibody in a biological sample obtained from a subject having an autoimmune disease (e.g., scleroderma) can indicate that the subject has a lower risk for cancer, while the presence of an anti-POLR3 antibody and the absence of an anti-RPA194 antibody in a biological sample obtained from the subject can indicate that the subject has a higher risk for cancer. As another example, the presence of an anti-RNPC-3 antibody in a biological sample obtained from a subject having an autoimmune disease (e.g., scleroderma) can indicate that the subject has a higher risk for cancer.

Having the ability to determine cancer risk in patients (e.g., patients with an autoimmune disease such as, but not limited to, scleroderma) provides a unique and unrealized opportunity to assess cancer risk of a scleroderma patient at the disease onset and throughout the disease course in unique serologic and phenotypic subsets relative to the general population. Simple, readily available measurements can be used to provide important information about the magnitude and specificity of cancer risk with the potential to improve risk stratification for cancer screening. In addition, the ability to predict increased or decreased cancer risk in patients enables care providers to begin early treatment for patients with increased cancer risk and/or to refrain from subjecting patients with decreased cancer risk to unnecessary treatment.

In general, one aspect of this document features a method for determining that a subject having an autoimmune disease is at a lower risk for cancer, where the method includes, or consists essentially of, detecting the presence of an anti-centromere antibody in a biological sample obtained from the subject, and determining that the subject has a lower risk for cancer when the anti-centromere antibody is detected. The autoimmune disease can be scleroderma. The lower risk for cancer can include a lower risk for having cancer. The lower risk for cancer can include a lower risk for developing cancer.

In another aspect, this document features a method for determining that a subject having an autoimmune disease is at a lower risk for cancer, where the method includes, or consists essentially of, detecting the presence of an anti-RNA polymerase III antibody and an anti-RPA194 antibody in a biological sample obtained from the subject, and determining that the subject has a lower risk for cancer when the presence of the anti-RNA polymerase III and the presence of the anti-RPA194 antibody is detected. The autoimmune disease can be scleroderma. The lower risk for cancer can include a lower risk for having cancer. The lower risk for cancer can include a lower risk for developing cancer.

In another aspect, this document features a method for determining that a subject having an autoimmune disease is at a higher risk for cancer, where the method includes, or consists essentially of, detecting the presence of an anti-RNA polymerase III and the absence of an anti-RPA194 antibody in a biological sample obtained from the subject, and determining that the subject has a higher risk for cancer when the presence of the anti-RNA polymerase III antibody and the absence of the anti-RPA194 antibody is detected. The autoimmune disease can be scleroderma. The higher risk for cancer can include a higher risk for having cancer. The higher risk for cancer can include a higher risk for developing cancer. The method also can include administering a therapeutic treatment to the subject. The therapeutic treatment can be adoptive T cell therapy, radiation therapy, surgery, a chemotherapeutic agent, an immune checkpoint inhibitor, a targeted therapy, a signal transduction inhibitor, a bispecific antibody, a monoclonal antibody, or any combination thereof.

In another aspect, this document features a method for treating cancer in a subject, where the method includes, or consists essentially of, identifying the subject as having cancer cells, and administering an anti-centromere antibody or antibody fragment to the subject, where the number of cancer cells within the subject is reduced. The cancer can be breast cancer, lung cancer, head and neck cancer, tongue cancer, prostate cancer, or melanoma. The subject can be a human. The subject can have an autoimmune disease. The autoimmune disease can be scleroderma, systemic lupus erythematosus, or myositis. For example, the autoimmune disease can be scleroderma. The antibody or antibody fragment can be a chimeric, humanized, or fully human antibody. The antibody fragment can include a Fab fragment, a Fab' fragment, a F(ab') fragment, or a scFv.

In another aspect, this document features a method for treating cancer in a subject, where the method includes, or consists essentially of, identifying the subject as having cancer cells, and administering to the subject an anti-RNA polymerase III antibody or antibody fragment and an anti-RPA194 antibody or antibody fragment, where the number of cancer cells within the subject is reduced. The cancer can be breast cancer, lung cancer, head and neck cancer, tongue cancer, prostate cancer, or melanoma. The subject can be a human. The subject can have an autoimmune disease. The autoimmune disease can be scleroderma, systemic lupus erythematosus, or myositis. For example, the autoimmune disease is scleroderma. The antibody or antibody fragment can be a chimeric, humanized, or fully human antibody. The antibody fragment can include a Fab fragment, a Fab' fragment, a F(ab') fragment, or a scFv.

In another aspect, this document features a method for treating cancer in a subject, where the method includes, or consists essentially of, identifying the subject as having cancer cells, and inducing an immune response in the subject by administering an antigen comprising a centromere or fragment thereof, where the administered antigen induces the immune response in the subject, and where the number of cancer cells within the subject is reduced. The cancer can be breast cancer. The subject can be a human. The subject can have an autoimmune disease. The autoimmune disease can be scleroderma, systemic lupus erythematosus, or myositis. For example, the autoimmune disease can be scleroderma.

In another aspect, this document features a method for treating cancer in a subject, where the method includes, or consists essentially of, identifying the subject as having cancer cells, and inducing an immune response in the subject by administering an antigen including RNA polymerase III or a fragment thereof and an antigen including RPA194 or a fragment thereof, where the administered antigens induce the immune response in the subject, and where the number of cancer cells within the subject is reduced. The cancer can be breast cancer. The subject can be a human. The subject can have an autoimmune disease. The autoimmune disease can be scleroderma, systemic lupus erythematosus, or myositis. For example, the autoimmune disease can be scleroderma.

In another aspect, this document features a method for selecting a subject for increased monitoring, where the method includes, or consists essentially of, detecting the absence of an anti-centromere antibody in a biological sample obtained from the subject, and selecting the subject for increased monitoring when the absence of the anti-centromere antibody is detected.

In another aspect, this document features a method for selecting a subject for further diagnostic testing, where the method includes, or consists essentially of, detecting the absence of an anti-centromere antibody in a biological sample obtained from the subject, and selecting the subject for further diagnostic testing when the absence of the anti-centromere antibody is detected.

In another aspect, this document features a method for selecting a subject for increased monitoring, where the method includes, or consists essentially of, detecting the presence of an anti-RNA polymerase III antibody in a biological sample obtained from the subject, detecting the absence of an anti-RPA194 antibody in a biological sample obtained from the subject, and selecting the subject for increased monitoring when the presence of the anti-RNA polymerase III antibody detected and the absence of the anti-RPA194 antibody is detected.

In another aspect, this document features a method for selecting a subject for further diagnostic testing, where the method includes, or consists essentially of, detecting the presence of an anti-RNA polymerase III antibody in a biological sample obtained from the subject, detecting the absence of an anti-RPA194 antibody in a biological sample obtained from the subject, and selecting the subject for further diagnostic testing when the presence of the anti-RNA polymerase III antibody detected and the absence of the anti-RPA194 antibody is detected.

In another aspect, this document features a method for determining that a subject having an autoimmune disease is at a higher risk for cancer, where the method includes, or consists essentially of, detecting the presence of an anti-RNPC-3 antibody in a biological sample obtained from the subject, and determining that the subject has a higher risk for cancer when the anti-RNPC-3 antibody is detected. The autoimmune disease can be scleroderma. The higher risk for cancer can include a higher risk for having cancer. The higher risk for cancer can include a higher risk for developing cancer. The method also can include administering a therapeutic treatment to the subject. The therapeutic treatment can be adoptive T cell therapy, radiation therapy, surgery, a chemotherapeutic agent, an immune checkpoint inhibitor, a targeted therapy, a signal transduction inhibitor, a bispecific antibody, a monoclonal antibody, or any combination thereof.

In another aspect, this document features a method for determining that a subject having an autoimmune disease is at a lower risk for cancer, where the method includes, or consists essentially of, detecting the absence of an anti-RNPC-3 antibody in a biological sample obtained from the subject, and determining that the subject has a lower risk for cancer when the absence of the anti-RNPC-3 antibody is detected. The autoimmune disease can be scleroderma. The lower risk for cancer can include a lower risk for having cancer. The lower risk for cancer can include a lower risk for developing cancer.

In another aspect, this document features a method for selecting a subject for increased monitoring, where the method includes, or consists essentially of, detecting the presence of an anti-RNPC-3 antibody in a biological sample obtained from the subject, and selecting the subject for increased monitoring when the anti-RNPC-3 antibody is detected.

In another aspect, this document features a method for selecting a subject for further diagnostic testing, where the method includes, or consists essentially of, detecting the presence of an anti-RNPC-3 antibody in a biological sample obtained from the subject, and selecting the subject for further diagnostic testing when the anti-RNPC-3 antibody is detected.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

is presented with 95% confidence intervals (shaded blue region). Red lines in each plot represent the expected cumulative incidence of cancer based on SEER data for the general population. Patients with scleroderma (All group), in particular those with topo antibodies, do not have a significantly increased risk of cancer over time compared to the general population. Scleroderma patients with anti-centromere antibodies appear to be protected from cancer. Scleroderma patients with pol III antibodies may have an increased risk of other cancers at disease onset. CTP-Negative patients have an increased risk of cancer that is notable at the time of scleroderma onset.

Figure 5:
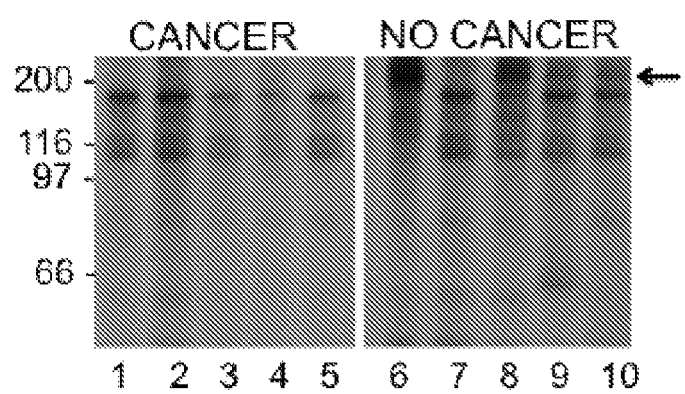

FIG. 5 is a comparison of immunoprecipitation (IP) profiles obtained using anti-POLR3 positive sera from SSc patients with or without cancer. IPs were performed from labeled lysates using sera from 10 anti-POLR3 positive SSc patients. 5 patients had an associated cancer (lanes 1-5), and 5 did not (lanes 6-10). The arrow marks an ~200 kDa band detected only in IPs from the no cancer set, which has been identified as anti-RPA194.

Figure 6:
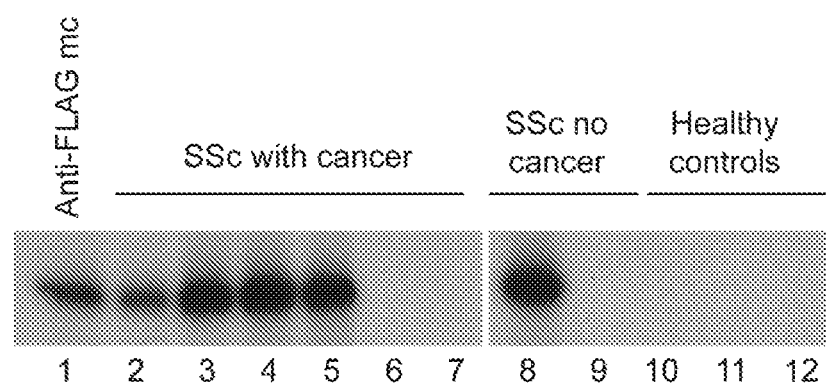

FIG. 6 shows detection of antibodies against RNPC3 by immunoprecipitation with 35S-methionine-labeled RNPC3. Sera from CTP-negative scleroderma patients with an associated cancer (lanes 2-7), CTP-negative scleroderma patients without an associated cancer (lanes 8 & 9) and healthy control subjects (lanes 10-12) were used to immunoprecipitate $^{35}$S-methionine radiolabeled full-length human RNPC3 generated by in vitro transcription and translation. For each set of immunoprecipitations performed, a positive reference immunoprecipitation was included using an anti-FLAG monoclonal antibody (lane 1; the RNPC3 is FLAG-tagged). The scleroderma sera shown in lanes 2-5 and lane 8 have antibodies against RNPC3.

Figure 7:
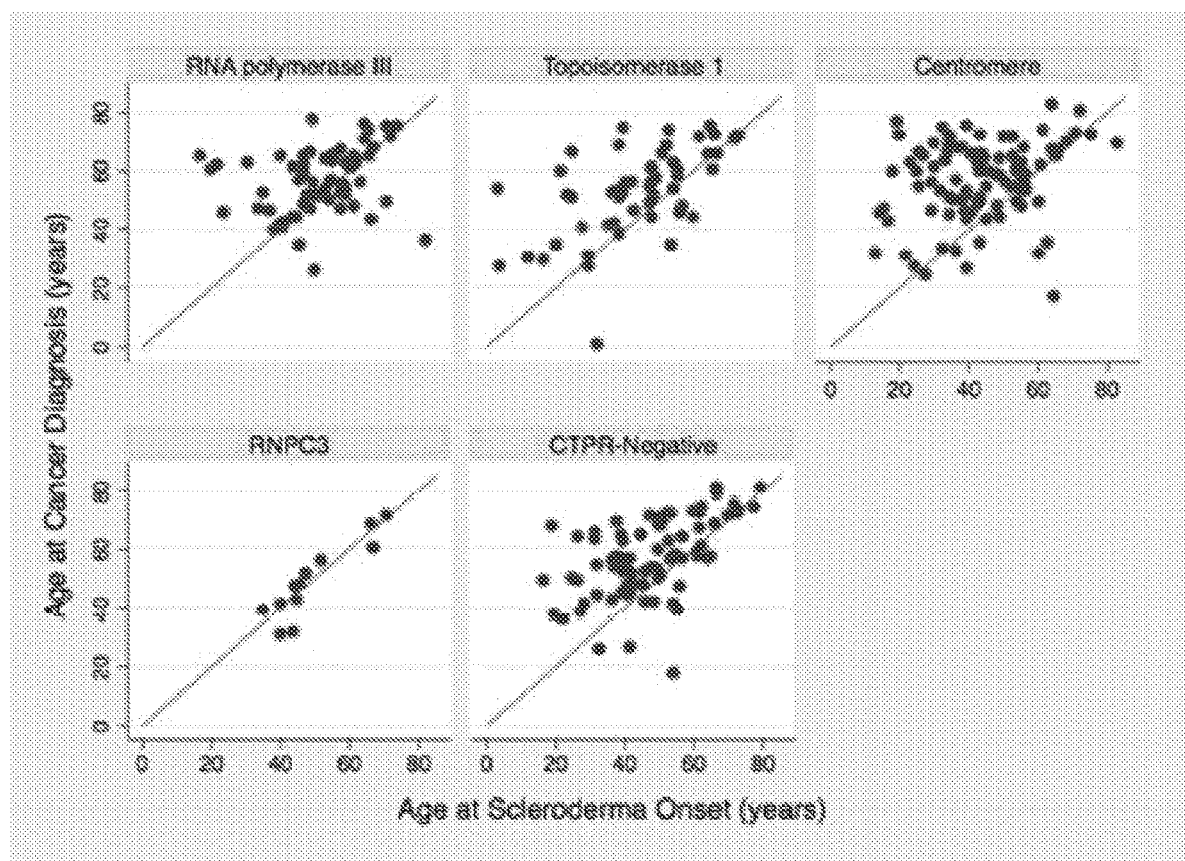

FIG. 7 contains scatterplots showing a relationship between age at cancer diagnosis and age at scleroderma onset. The line in each graph denotes perfect agreement between age at cancer diagnosis and age at scleroderma onset. CTPR-Negative refers to the group that is negative for centromere, topoisomerase 1, RNA polymerase III and RNPC3 autoantibodies. As shown in the Figure, patients with anti-RNPC3 or anti-POLR3 antibodies are more likely to have cancer coincide with scleroderma onset.

Figure 8:
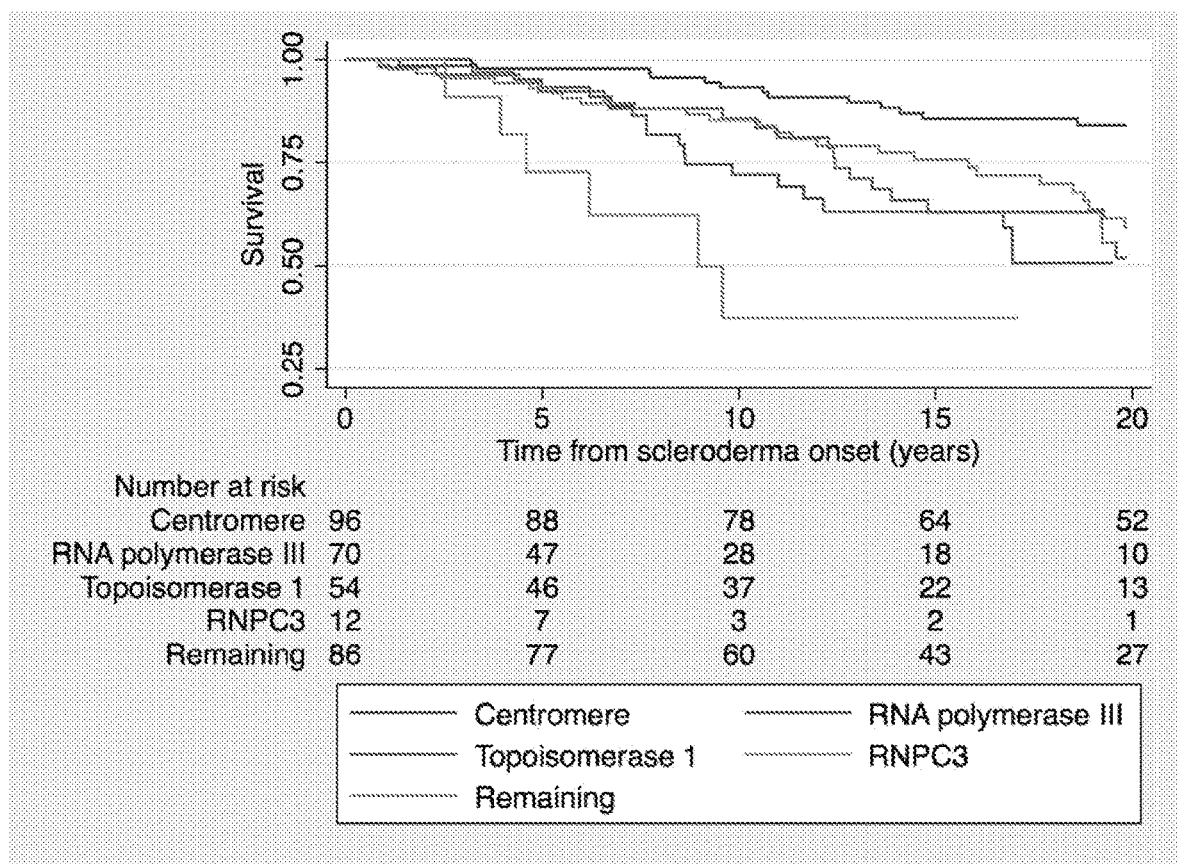

FIG. 8 shows that, among patients with scleroderma and cancer, patients with RNPC3 autoantibodies had significantly poorer survival (median survival 9.0 years in anti-RNPC3 vs. >20 years in all other antibody groups; log rank test p<0.0001).

DETAILED DESCRIPTION

Patients with autoimmune diseases (e.g., scleroderma and other autoimmune rheumatic diseases) have distinctive autoantibodies that associate with unique clinical phenotypes. For example, the presence or absence of autoantibodies in scleroderma patients can predict increased or decreased cancer risk as compared to the general population.

This document provides materials and methods for assessing the cancer risk of subjects (e.g., humans) having autoimmune diseases (e.g., scleroderma) as compared to the general population (e.g., healthy patients and/or patients that do not have an autoimmune disease). The cancer risk (e.g., a lower cancer risk or a higher cancer risk) of a subject having an autoimmune disease can be determined based, at least in part, on the presence or absence of one or more antibodies in a sample obtained from the subject. In some cases, the materials and methods described herein can be used to determine that a subject (e.g., a subject having an autoimmune disease) has a higher cancer risk (e.g., a higher risk for having cancer or a higher risk for developing cancer). An antibody that is associated with one or more autoimmune diseases (e.g., scleroderma) can be any appropriate antibody. In some cases, the antibody can be an autoantibody. In some cases, antibodies can be scleroderma-specific autoantibodies. In some cases, antibodies can be cross-reactive antibodies. Examples of antibodies that are associated with the risk of cancer in subjects having one or more autoimmune diseases include, without limitation, anti-centromere antibodies, anti-POLR3 antibodies, anti-RPA194 antibodies, and/or anti-RNPC-3 antibodies. Exemplary anti-centromere antibodies, anti-POLR3 antibodies, anti-RPA194 antibodies, and/or anti-RNPC-3 antibodies are described in, for example, Example 1 and Example 2.

This document also provides materials and methods for treating subjects (e.g., humans, such as humans having autoimmune diseases) identified as having a higher risk for cancer and/or identified as having cancer as described herein. For example, one or more antibodies described herein (e.g., anti-centromere antibodies and/or anti-RPA194 antibodies) can be administered to a subject identified as having a higher risk for cancer and/or identified as having a cancer as described herein to treat the subject. In some cases, treating a subject identified as having a higher risk for cancer can be effective to slow or prevent development of a cancer. In some cases, treating a subject identified as having cancer can be effective to reduce or eliminate the number of cancer cells within the subject. In some cases, materials and methods described herein also can include identifying the subject as having a higher risk for cancer and/or identifying the subject as having cancer.

Any type of subject can be assessed and/or treated as described herein. In some cases, a subject can be a mammal. Examples of mammals that can be assessed and/or treated as described herein include, without limitation, primates (e.g., humans and non-human primates such as chimpanzees, baboons, or monkeys), dogs, cats, pigs, sheep, rabbits, mice, and rats. For example, the subject can be a human. In some cases, humans having an autoimmune disease (e.g., scleroderma) can be assessed for cancer risk as described herein. For example, the presence or absence of one or more antibodies described herein (e.g., anti-centromere antibodies, anti-POLR3 antibodies, anti-RPA194 antibodies, and/or anti-RNPC-3 antibodies) in a sample obtained from a human having scleroderma can be used to determine the cancer risk of the human having scleroderma. In some cases, humans identified as having a higher risk of cancer as described herein and/or identified as having cancer can be treated. For example, one or more antibodies described herein (e.g., anti-centromere antibodies and/or anti-RPA194 antibodies) can be administered to a subject identified as having a higher risk for cancer and/or identified as having a cancer to treat the subject.

When assessing the cancer risk of a subject (e.g., a human) having an autoimmune disease as described herein, the autoimmune disease can be any autoimmune disease. In some cases, an autoimmune disease can be a cancer-associated rheumatic syndrome. Examples of autoimmune diseases that can assessed described herein include, without limitation, scleroderma, systemic lupus erythematosus (SLE), myositis, Sjogren's syndrome, and vasculitis. In some cases, materials and methods described herein can be used to assess the cancer risk of a subject having scleroderma.

Any appropriate method can be used to identify a subject having an autoimmune disease. Examples of methods that can be used to identify subjects (e.g., humans) having an autoimmune disease include, without limitation, autoantibody (e.g., antinuclear) tests, physical examination (e.g., for autoimmune tissue damage such as Raynaud's phenomenon, rash, and arthritis), genetic screening, clinical history (e.g., renal disease), and imaging techniques (e.g., magnetic resonance imaging (MRI), ultrasound, and x-rays).

Any appropriate sample from a subject can be used to detect the presence or absence of one or more antibodies described herein (e.g., anti-centromere antibodies, anti-POLR3 antibodies, anti-RPA194 antibodies, and/or anti-RNPC-3 antibodies) in the subject (e.g., a human). For example, biological samples such as fluid samples (e.g., blood, serum, or plasma) can be obtained from a human, and the presence or absence of one or more anti-centromere antibodies, anti-POLR3 antibodies, anti-RPA194 antibodies, and/or anti-RNPC-3 antibodies can be detected. In some cases, a blood sample can be obtained from a subject and used to detect the presence or absence of one or more anti-centromere antibodies, anti-POLR3 antibodies, anti-RPA194 antibodies, and/or anti-RNPC-3 antibodies. In some cases, a serum sample can be obtained from a subject and used to detect the presence or absence of one or more anti-centromere antibodies, anti-POLR3 antibodies, anti-RPA194 antibodies, and/or anti-RNPC-3 antibodies. In some cases, a plasma sample can be obtained from a subject and used to detect the presence or absence of one or more anti-centromere antibodies, anti-POLR3 antibodies, anti-RPA194 antibodies, and/or anti-RNPC-3 antibodies.

Any appropriate method can be used to detect the presence or absence of one or more antibodies described herein (e.g., anti-centromere antibodies, anti-POLR3 antibodies, anti-RPA194 antibodies, and/or anti-RNPC-3 antibodies). Methods of detecting the presence or absence of an antibody include, without limitation, immunoprecipitation (IP), western blotting, ELISA assays, line immunoassays, and electrochemiluminesence assays. In some cases, the presence of an antibody can be any detectable level of the antibody. In some cases, the presence of an antibody can be any detectable level that is higher than a reference level of an antibody. In some cases, the presence of an antibody can be a detectable level that is at least 1, 2, 3, 4, 5, or more standard deviations above a reference level of the antibody. In some cases, the absence of an antibody can be any non-detectable level of the antibody. In some cases, the absence of an antibody can be any level that is about the same or lower than a reference level of an antibody. In some cases, a reference level of an antibody can be the level of the antibody present in a reference subject that does not exhibit the autoimmune disorder. In some cases, a reference level of an antibody can be the level of the antibody present in the subject prior to onset of the autoimmune disorder.

Once the presence or absence of one or more antibodies described herein (e.g., anti-centromere antibodies, anti-POLR3 antibodies, anti-RPA194 antibodies, and/or anti-RNPC-3 antibodies) has been detected in a sample (e.g., a biological sample) obtained from a subject, the subject can be assessed to determine the cancer risk of the subject and/or to select a treatment option for the subject (e.g., therapeutic intervention, increased monitoring, and/or further diagnostic testing).

In some cases, the presence or absence of one or more anti-centromere antibodies in a sample obtained from a subject having an autoimmune disease (e.g., scleroderma) can be used to determine the cancer risk of the subject. For example, the presence of an anti-centromere antibody in a biological sample obtained from a subject having an autoimmune disease (e.g., scleroderma) can indicate that the subject has a lower risk for cancer. As another example, the absence of an anti-centromere antibody in a biological sample obtained from a subject having an autoimmune disease (e.g., scleroderma) can indicate that the subject has a higher risk for cancer.

In some cases, the presence or absence of one or more anti-POLR3 antibodies and one or more anti-RPA194 antibodies in a sample obtained from a subject having an autoimmune disease (e.g., scleroderma) can be used to determine the cancer risk of the subject. For example, the presence of an anti-POLR3 antibody and an anti-RPA194 antibody in a biological sample obtained from the subject having an autoimmune disease (e.g., scleroderma) can indicate that the subject has a lower risk for cancer. As another example, the presence of an anti-POLR3 antibody and the absence of an anti-RPA194 antibody in a biological sample obtained from the subject having an autoimmune disease (e.g., scleroderma) can indicate that the subject has a higher risk for cancer.

In some cases, the presence or absence of one or more anti-RNPC-3 antibodies in a sample obtained from a subject having an autoimmune disease (e.g., scleroderma) can be used to determine the cancer risk of the subject. For example, the presence of an anti-RNPC-3 antibody in a biological sample obtained from a subject having an autoimmune disease (e.g., scleroderma) can indicate that the subject has a higher risk for cancer. As another example, the absence of an anti-RNPC-3 antibody in a biological sample obtained from a subject having an autoimmune disease (e.g., scleroderma) can indicate that the subject has a lower risk for cancer.

When a subject having an autoimmune disease (e.g., scleroderma) is identified as having higher risk for cancer, based, at least in part, on the presence or absence of one or more antibodies described herein (e.g., anti-centromere antibodies, anti-POLR3 antibodies, anti-RPA194 antibodies, and/or anti-RNPC-3 antibodies) in a sample obtained from the subject, the subject can be selected for therapeutic intervention (e.g., the subject can be administered one or more antibodies described herein (e.g., anti-centromere antibodies and/or anti-RPA194 antibodies) and/or one or more therapeutic agents to treat cancer)). In some cases, the subject can be administered or instructed to self-administer anti-centromere antibodies and/or anti-RPA194 antibodies. For example, when the absence of an anti-centromere antibody is detected in a biological sample obtained from a subject having an autoimmune disease (e.g., scleroderma), the subject can be administered or instructed to self-administer one or more anti-centromere antibodies. As another example, when the absence of an anti-RPA194 antibody is detected in a biological sample obtained from a subject (e.g., a subject having scleroderma and anti-POLR3 antibodies), the subject can be administered one or more anti-RPA194 antibodies. In some cases, anti-centromere antibodies and/or anti-RPA194 antibodies can be administered together with one or more compounds (e.g., other compounds that target other RNA polymerase components). For example, anti-centromere antibodies can be administered together with one or more compounds that target components of RNA polymerase 3 (POL3) and/or RNA polymerase I (POL1). In some cases, the subject can be administered or instructed to self-administer one or more therapeutic agents to treat cancer. Examples of therapeutic agents that can be used to treat cancer include, without limitation, adoptive T cell therapy (e.g., chimeric antigen receptors and/or T cells having wild-type or modified T cell receptors), radiation therapy, surgery, a chemotherapeutic agent, an immune checkpoint inhibitor, a targeted therapy (e.g., kinase inhibitors (e.g., kinase inhibitors that target a particular genetic lesion, such as a translocation or mutation)), a signal transduction inhibitor, a bispecific antibody, a monoclonal antibody. In cases where one or more antibodies described herein are used in combination with one or more therapeutic agents to treat cancer, the one or more antibodies can be administered at the same time or independently of the administration of one or more therapeutic agents. For example, the one or more antibodies can be administered before, concurrent with, or after the one or more therapeutic agents are administered.

When a subject having an autoimmune disease (e.g., scleroderma) is identified as having higher risk for cancer, based, at least in part, on the presence or absence of one or more antibodies described herein (e.g., anti-centromere antibodies, anti-POLR3 antibodies, anti-RPA194 antibodies, and/or anti-RNPC-3 antibodies) in a sample obtained from the subject, the subject can be selected for increased monitoring and/or for further diagnostic testing. Examples of increased monitoring can include, without limitation, undergoing more frequent cancer screening including, but not limited to, imaging techniques (e.g., mammograms, ultrasounds, computed tomography (CT) scans, MRIs, and nuclear medicine modalities such as whole body PET/CT), physical examination (e.g., laryngoscopy, upper endoscopy, flexible sigmoidoscopy, and colonoscopy), and/or laboratory tests (e.g., circulating tumor cells analyses and liquid DNA biopsies). In some cases, the subject is selected for increased monitoring for a particular cancer. For example, increased monitoring for breast cancer can include more frequent and/or alternating MRI and mammograms. As another example, increased monitoring for lung cancer can include obtaining and investigating more frequent chest CT images. As another example, increased monitoring for tongue cancer can include more frequent physical examinations. As another example, increased monitoring for prostate cancer can include more frequent PSA tests. In cases where the absence of an anti-centromere antibody is detected in a biological sample obtained from a subject having an autoimmune disease (e.g. scleroderma), the subject can be selected for increased monitoring and/or for further diagnostic testing. In cases where the presence of an anti-POLR3 antibody is detected and the absence of an anti-RPA194 antibody is detected in a biological sample obtained from a subject having an autoimmune disease (e.g. scleroderma), the subject can be selected for increased monitoring and/or for further diagnostic testing. In cases where the presence of an anti-RNPC-3 antibody is detected in a biological sample obtained from a subject having an autoimmune disease (e.g. scleroderma), the subject can be selected for increased monitoring and/or for further diagnostic testing.

In some cases, a subject that has cancer can be treated using the materials and methods described herein. Any appropriate method can be used to identify a subject having cancer. For example, imaging techniques, biopsy techniques, blood tests, urine tests, genetic tests (e.g., cytogenetics and fluorescent in situ hybridization ("FISH")) can be used to identify subjects (e.g., humans) having cancer.

Once a subject having an autoimmune disease (e.g. scleroderma) is identified as having cancer, the subject can be administered or instructed to self-administer one or more antibodies described herein (e.g., anti-centromere antibodies and/or anti-RPA194 antibodies). In some cases, an antibody described herein can induce immune response that can treat a cancer. For example, anti-centromere antibodies and/or anti-RPA194 antibodies can be administered to treat a cancer by inducing an immune response (e.g., an anti-cancer immune response). Exemplary anti-centromere antibodies and/or anti-RPA194 antibodies can be as described in, for example, Example 1 and Example 2.

As used herein, the term "antibody" includes whole antibodies and antibody fragments and derivatives provided that the fragment or derivative maintains the ability to treat cancer (e.g., by inducing an immune response such as an anti-cancer immune response). Examples of antibody fragments include, without limitation, single-chain variable fragments (scFvs), antigen-binding (Fab) fragments (e.g., Fab' or (Fab)$_2$), Fv fragments, polyclonal antibodies, monoclonal antibodies, bispecific antibodies, diabodies, and other antibody-like molecules. An antibody, antibody fragment, or antibody derivative can be of any class (e.g., IgGs IgA, IgM). In some cases, an antibody, antibody fragment, or antibody derivative fragment can be chimeric. In some cases, an antibody, antibody fragment, or antibody derivative can be humanized. In some cases, an antibody, antibody fragment, or antibody derivative can be human antibody, antibody fragment, or antibody derivative.

When treating a subject (e.g., a human) identified as having higher risk of cancer and/or identified as having cancer as described herein, the cancer can be any appropriate cancer. Examples of cancers include, without limitation, breast cancer, lung cancer, head and neck cancer, tongue cancer, prostate cancer, and melanoma. In some cases, materials and methods described herein can be used to slow or prevent development of breast cancer in a human having scleroderma and identified as having higher risk of breast cancer.

In some cases, one or more antibodies (e.g., anti-centromere antibodies and/or anti-RPA194 antibodies) can be administered to a subject (e.g., a subject identified as having higher risk of cancer and/or identified as having cancer as described herein) once or multiple times over a period of time ranging from days to weeks. In some cases, one or more antibodies described herein can be formulated into a pharmaceutically acceptable composition for administration to a subject. For example, a therapeutically effective amount of anti-centromere antibodies and/or anti-RPA194 antibodies can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more antibodies described herein (e.g., anti-centromere antibodies and/or anti-RPA194 antibodies) can be designed for oral, parenteral (including subcutaneous, intramuscular, intravenous, and intradermal), or intratumoral administration.

Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more antibodies described herein (e.g., anti-centromere antibodies and/or anti-RPA194 antibodies) can be administered locally (e.g., intratumorally) or systemically. For example, a composition provided herein can be administered locally by injection into tumors or into biological spaces infiltrated by tumors (e.g. peritoneal cavity and/or pleural space). In some cases, a composition provided herein can be administered systemically, orally, or by injection to a subject (e.g., a human).

Effective doses can vary depending on the risk and/or the severity of the cancer, the route of administration, the age and general health condition of the subject, excipient usage, the possibility of co-usage with other therapeutic treatments such as use of other agents, and the judgment of the treating physician.

An effective amount of a composition containing one or more antibodies described herein (e.g., anti-centromere antibodies and/or anti-RPA194 antibodies) can be any amount that reduces the number of cancer cells present within the subject without producing significant toxicity to the subject.

If a particular subject fails to respond to a particular amount, then the amount of one or more antibodies described herein (e.g., anti-centromere antibodies and/or anti-RPA194 antibodies) can be increased (e.g., by two-fold, three-fold, four-fold, or more). After receiving this higher amount, the subject can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of one or more antibodies described herein (e.g., anti-centromere antibodies and/or anti-RPA194 antibodies) can be any amount that reduces the number of cancer cells present within the subject without producing significant toxicity to the subject. For example, the frequency of administration of anti-centromere antibodies and/or anti-RPA194 antibodies can be from about two to about three times a week to about two to about three times a year. In some cases, a subject identified as having higher risk of cancer as described herein and/or identified as having cancer can receive a single administration of one or more antibodies described herein. The frequency of administration of one or more antibodies described herein can remain constant or can be variable during the duration of treatment. A course of treatment with a composition containing one or more antibodies described herein can include rest periods. For example, a composition containing one or more antibodies described herein can be administered every other month over a two-year period followed by a six-month rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more antibodies described herein (e.g., anti-centromere antibodies and/or anti-RPA194 antibodies) can be any duration that reduces the number of cancer cells present within the mammal without producing significant toxicity to the subject. In some cases, the effective duration can vary from several months to several years. In general, the effective duration for reducing the number of cancer cells present within the subject can range in duration from about one or two months to five or more years. Multiple factors can influence the actual effective duration used for a particular treatment. For example, an effective duration can vary with the frequency of administration, effective amount, use of multiple treatment agents, route of administration, and severity of the condition being treated.

In certain instances, the number of cancer cells present within a subject can be monitored. Any appropriate method can be used to determine whether or not the number of cancer cells present within a subject is reduced. For example, imaging techniques or laboratory assays can be used to assess the number of cancer cells present within a subject.

The invention will be further described in the following examples, which do not limit the scope of the invention described in the claims.

EXAMPLES

Example 1: Autoantibodies and Scleroderma Phenotype Define Subgroups at High-Risk or Low-Risk for Cancer Cancer risk at scleroderma onset was examined in distinct serologic and phenotypic subsets relative to the general population. Three novel findings were demonstrated: (i) anti-pol patients are at increased risk for different types of cancer at scleroderma onset depending on whether they have limited or diffuse cutaneous disease; (ii) patients who are CTP-negative also have an increased cancer risk at scleroderma onset; and (iii) patients with anti-centromere antibodies are protected against cancer. These results suggested that this immune response can have potent anti-cancer effects, and that this subgroup or patients can represent the boundary condition for the scleroderma spectrum, where cancer induces the immune response which is almost completely effective in controlling the cancer. These findings can be used to develop guidelines for cancer screening in patients with new onset scleroderma.

Methods

Study Population

Patients seen at the Johns Hopkins Scleroderma Center for their first visit between Jan. 1, 2000 and Dec. 31, 2015 were eligible for the study if they provided IRB-approved consent and had a diagnosis of scleroderma. Scleroderma was defined by 1980 or 2013 ACR/EULAR classification criteria (Subcommittee for scleroderma criteria of the American Rheumatism Association Diagnostic and Therapeutic Criteria Committee, 1980, *Arthritis & Rheumatism*, 23(5):581-90; and van den Hoogen et al., 2013, *Arthritis & Rheumatism*, 65(11):2737-47), at least 3 of 5 CREST (calcinosis, Raynaud's phenomenon, esophageal dysmotility, sclerodactyly, telangiectasia) syndrome criteria, or having definite Raynaud's, abnormal nailfold capillaries and a scleroderma-specific autoantibody. Clinical and serological data were collected prospectively at 6-month intervals in an IRB-approved database. Demographic data, disease onset dates, cutaneous subtype, and autoantibody status were abstracted from the database. Patients were classified as having limited or diffuse scleroderma by established criteria as described in, for example, LeRoy et al., 1988, *J. Rheumatol.*, 15(2):202-5. Four autoantibody categories were assessed: anti-centromere, anti-topoisomerase-1 (topo), anti-pol, and CTP-negative. Patients who could not be classified into an autoantibody subset because of missing autoantibody data were included in the overall scleroderma cohort analyses only. For all analyses, the timing of scleroderma onset was defined by the first scleroderma symptom, either Raynaud's or non-Raynaud's. Patient reported cancer diagnoses and dates of diagnosis were confirmed by medical record review and pathology reports, if available, as described in, for example, Shah et al., 2015, *Arthritis & Rheumatology*, 67(4):1053-61. Electronic medical records were comprehensively reviewed for the entire study population to ensure that all cancer cases were captured.

Examination of Cancer Risk

Cancer incidence was examined in the overall scleroderma cohort, and in autoantibody and cutaneous subsets. Cancer risk was determined by comparing cancer incidence in our cohort with the Surveillance, Epidemiology and End Results (SEER) registry, a nationally representative sample of the US population. Standardized incidence ratios (SIR) for cancer overall and individual cancer types were computed. Primary analyses focused on breast and lung cancers as these are the most prevalent cancers in scleroderma, but other cancer sites were also examined. The observed number of cancers in our cohort were compared with the expected number of cancer cases for the study population at risk by identifying the crude rate of cancer incidence corresponding to each patient's age, gender, race, ethnicity and the calendar year of exposure in SEER (www.seer.cancer.gov/). Person time prior to 1973 was not examined as SEER data begins in 1973. At the time of analysis, SEER data were complete through the year 2012. SEER crude rates for 2012 were used as a surrogate for person time after 2012. The sum of the crude rates for all years of exposure for all patients yielded the expected number of cancer cases. To find the 95% confidence limits, the procedure based on the Poisson distribution model for the analysis of cancer incidence rates we followed as described in, for example, Sahai et al., 1993, *Biometrical J.*, 35(7):857-67).

To determine if cancer diagnosed close to the time of scleroderma onset may be suggestive of cancer-induced autoimmunity, two time windows were examined: (i) 3 years before scleroderma onset until cancer diagnosis date or the last visit date (i.e., -3 years onwards or "overall cancer risk") and (ii) 3 years before scleroderma onset until 3 years after scleroderma onset (i.e., ±3 years or "cancer-associated scleroderma"). Patients with cancers preceding the start of these time windows were excluded from our analysis. The study population for our primary analyses comprised 2383 scleroderma patients.

Since including individuals with cancers diagnosed a few years prior to joining the cohort may introduce a form of immortal person time bias, an additional analysis restricting the study population to patients who presented to our Center within 5 years of their first scleroderma symptom ("recent onset scleroderma") was performed. Patients who had a cancer diagnosis prior to presentation and only included cancer diagnoses that occurred after the first visit to our scleroderma center were excluded. As referral to a tertiary center is often delayed, an analysis involving patients with new onset scleroderma and examined cancer diagnoses after scleroderma symptom onset was also performed.

Cancer risk over time was examined and time-dependent SIR plots centered at the time of scleroderma onset were generated. These plots examined cancer risk in 6-year time windows (i.e. ±3 years). Only patients who have not been diagnosed with cancer at the beginning of each six-year time period were considered. These periods ended on the date of cancer diagnosis, last visit or at the end of the six-year window.

Results

The study population for our primary analyses consisted of 2383 scleroderma patients contributing 36,361 person-years (Table 1). The mean age at scleroderma onset was 42.4±15.1 years. Sixty percent of patients had limited scleroderma, 83% were female, and 76% self-identified as white race. Six hundred eight patients (25%) were positive for anti-centromere (centromere) antibodies, 481 (20%) for anti-topo, and 278 (11%) for anti-pol; 379 patients (15%) were CTP-negative. An additional 671 patients could not be classified into an antibody subset because of missing autoantibody data. Approximately ten percent of patients ($232/2383$) had a history of cancer.

TABLE 1

| | | | Risk for all cancers.* | | | | |
|---|---|---|---|---|---|---|---|
| Analysis time | Antibody | Subtype | Person-years | No. observed | No. expected | SIR (95% CI) | p-value |
| Overall risk | All | all | 36,361 | 232 | 237.6 | 0.98 (0.85-1.11) | 0.75 |
| | | limited | 25,826 | 145 | 173.4 | 0.84 (0.71-0.98) | <0.05 |
| | | diffuse | 10,535 | 87 | 64.2 | 1.35 (1.08-1.67) | <0.01 |
| | Centromere | all | 12,261 | 60 | 91.3 | 0.66 (0.50-0.85) | <0.001 |
| | | limited | 11,527 | 56 | 86.1 | 0.65 (0.49-0.84) | <0.001 |
| | | diffuse | 734 | 4 | 5.2 | 0.76 (0.21-196) | 0.80 |
| | Topo | all | 6,844 | 45 | 40.2 | 1.12 (0.82-1.50) | 0.49 |
| | | limited | 3,855 | 25 | 23.5 | 1.06 (0.69-1.57) | 0.82 |
| | | diffuse | 2,989 | 20 | 16.7 | 1.20 (0.73-1.86) | 0.47 |

TABLE 1-continued

Risk for all cancers.*

| Analysis time | Antibody | Subtype | Person-years | No. observed | No. expected | SIR (95% CI) | p-value |
|---|---|---|---|---|---|---|---|
| | Pol III | all | 3,262 | 49 | 22.2 | 2.21 (1.63-2.92) | <0.001 |
| | | limited | 920 | 11 | 6.3 | 1.74 (0.87-3.11) | 0.12 |
| | | diffuse | 2,342 | 38 | 15.8 | 2.40 (1.70-3.29) | <0.001 |
| | CTP-Negative | all | 5,487 | 47 | 33.5 | 1.40 (1.03-1.86) | <0.05 |
| | | limited | 3,889 | 37 | 23.9 | 1.55 (1.09-2.14) | <0.05 |
| | | diffuse | 1,598 | 10 | 9.7 | 1.03 (0.49-1.90) | 0.99 |
| ±3 years | All | all | 13,097 | 81 | 69.1 | 1.17 (0.93-1.46) | 0.17 |
| | | limited | 7,906 | 36 | 41.1 | 0.88 (0.61-1.21) | 0.48 |
| | | diffuse | 5,191 | 45 | 27.9 | 1.61 (1.17-2.15) | <0.01 |
| | Centromere | all | 3,206 | 11 | 17.7 | 0.62 (0.31-1.11) | 0.12 |
| | | limited | 2,994 | 11 | 16.6 | 0.66 (0.33-1.18) | 0.20 |
| | | diffuse | 212 | 0 | 1.1 | 0.00 (0.00-334) | 0.66 |
| | Topo | all | 2,735 | 13 | 13.0 | 1.00 (0.53-1.72) | 0.99 |
| | | limited | 1,344 | 4 | 6.5 | 0.61 (0.17-1.56) | 0.44 |
| | | diffuse | 1,391 | 9 | 6.4 | 1.41 (0.64-2.67) | 0.39 |
| | Pol III | all | 1,499 | 29 | 9.7 | 2.99 (2.00-4.29) | <0.001 |
| | | limited | 303 | 3 | 1.9 | 1.61 (0.33-4.70) | 0.57 |
| | | diffuse | 1,196 | 26 | 7.8 | 3.32 (2.17-4.86) | <0.001 |
| | CTP-Negative | all | 2,135 | 20 | 10.3 | 1.94 (1.19-3.00) | <0.01 |
| | | limited | 1,330 | 15 | 6.1 | 2.45 (1.37-4.04) | <0.01 |
| | | diffuse | 805 | 5 | 4.2 | 1.20 (0.39-2.80) | 0.81 |

*Excluding non-melanoma skin cancers.

All Cancers

Among all scleroderma patients (Table 1, overall cancer risk), an increased risk of cancer was not appreciated compared to the general US population (SIR 0.98, 95% CI 0.85-1.11). Patients with diffuse scleroderma had a 35% higher risk of cancer (SIR 1.35, 95% CI 1.08-1.67), whereas patients with limited scleroderma had a 16% lower risk of cancer (SIR 0.84, 95% CI 0.71-0.98). The increased risk of cancer was most notable among anti-pol patients (SIR 2.21, 95% CI 1.63-2.92) and CTP-negative patients (SIR 1.40, 95% CI 1.03-1.86). In contrast, patients with anti-centromere were protected from cancer (SIR 0.66, 95% CI 0.50-0.85).

Next, the risk of cancer within 3 years of scleroderma onset (i.e., "cancer-associated scleroderma") was determined. Patients with diffuse scleroderma had a 61% increased risk compared to the general population (SIR 1.61, 95% CI 1.17-2.15). This risk was increased among anti-pol patients (SIR 2.99, 95% CI 2.00-4.29), particularly those with diffuse disease (SIR 3.32, 95% CI 2.17-4.86). Additionally, CTP-negative patients had an increased risk of cancer-associated scleroderma (SIR 1.94, 95% CI 1.19-3.00), especially those with limited disease (SIR 2.45, 95% CI 1.37-4.04).

Figure 1:
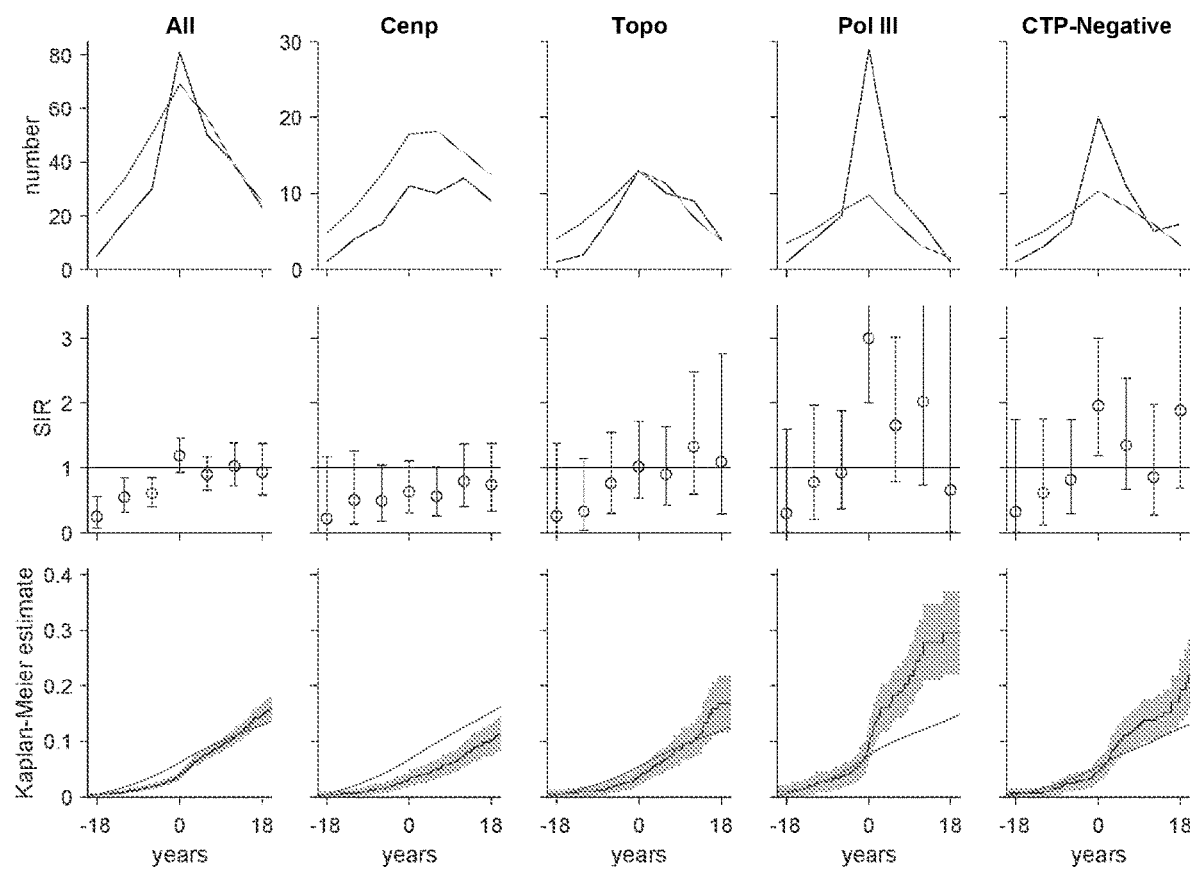
FIG. 1 shows scleroderma patient risk of all cancers (excluding non-melanoma skin cancers) over time. In each graph, the x-axis reflects time from scleroderma onset (defined as time zero); negative time is time before the 1st scleroderma symptom, and positive time is time after the 1st scleroderma symptom. Top row, the observed number of cancer cases (blue) is presented in comparison with the number of cancer cases that are expected based on SEER data (red). Middle row, the ratio between the observed and expected cancer cases is presented as a standardized incidence ratio (SIR) along with its 95% confidence interval. Values of 1 denote a cancer risk equivalent to that of the background population. Each time window represents a 6-year period (i.e. ±3 years) with the graph centered at time 0 (scleroderma onset). Bottom row, the cumulative incidence of cancer among scleroderma patients (solid blue line) is presented with 95% confidence intervals (shaded blue region). Red lines represent the expected cumulative incidence of cancer based on SEER data for the general population. Patients with scleroderma ("All" and "Topo" groups) do not have a significantly increased risk of cancer over time compared to the general population. Interestingly, scleroderma patients with anti-centromere antibodies appear to be protected from cancer. Scleroderma patients with pol III antibodies and the CTP-Negative group have an increased risk of cancer that is prominent at scleroderma onset. CTP-Negative refers to the group that is negative for centromere, topoisomerase 1, and RNA polymerase III autoantibodies. The cumulative incidence of cancer is significantly higher than that observed in the general population among patients with pol III autoantibodies.

The increased risk of cancer at the time of scleroderma onset among anti-pol-positive and CTP-negative patients is illustrated in FIG. 1. The number of cancer cases observed around the time of scleroderma onset (top row, blue curve) is greater than the number of expected cancer cases based on SEER data (red curve) in these two autoantibody subsets. The relative risk of cancer compared to the general population is presented in time-dependent SIRs (middle row) and was increased for anti-pol-positive and CTP-negative groups close to scleroderma onset. The cumulative incidence of cancer was significantly higher among anti-pol patients (blue lines, blue dashed lines 95% CI) compared to that expected in the general population (red line) (bottom row, FIG. 1). In contrast, the cumulative incidence of cancer was lower than expected in the anti-centromere group.

Cancer Risk in Patients with Recent Onset Scleroderma

To determine how these findings may impact the approach to cancer screening in patients with recent onset scleroderma, two additional analyses were performed restricting our study population to patients who presented to our scleroderma center within 5 years of their first scleroderma symptom and examined cancer diagnoses (i) after the first visit to the tertiary referral center or (ii) after the first scleroderma symptom. The findings of an increased risk of cancer among all patients with diffuse scleroderma, all anti-pol-positive patients, and anti-pol-positive patients with diffuse scleroderma remained unchanged in both analyses (Table 2). Interestingly, ~19 anti-pol patients need to be screened to identify one malignancy in the following 5 years at our tertiary referral center; this number is ~11 at community rheumatology practices.

TABLE 2

Risk for all cancers after 1st visit to Johns Hopkins Scleroderma Center and after 1st scleroderma symptom.*

| Analysis time | Antibody | Subtype | Person-years | No. observed | No. expected | SIR (95% CI) | p-value |
|---|---|---|---|---|---|---|---|
| After 1st visit | All | all | 4,900 | 54 | 40.5 | 1.33 (1.00-1.74) | <0.05 |
| | | limited | 2,271 | 20 | 19.5 | 1.03 (0.63-1.59) | 0.97 |
| | | diffuse | 2,629 | 34 | 21.0 | 1.62 (1.12-2.26) | <0.05 |

TABLE 2-continued

Risk for all cancers after 1st visit to Johns Hopkins Scleroderma Center and after 1st scleroderma symptom.*

| Analysis time | Antibody | Subtype | Person-years | No. observed | No. expected | SIR (95% CI) | p-value |
|---|---|---|---|---|---|---|---|
| | Cenp | all | 768 | 5 | 7.3 | 0.68 (0.22-1.59) | 0.52 |
| | | limited | 724 | 4 | 6.9 | 0.58 (0.16-1.48) | 0.36 |
| | | diffuse | 44 | 1 | 0.4 | 2.31 (0.06-12.89) | 0.70 |
| | Topo | all | 1,169 | 13 | 10.2 | 1.27 (0.68-2.17) | 0.46 |
| | | limited | 403 | 5 | 3.9 | 1.29 (0.42-3.01) | 0.69 |
| | | diffuse | 766 | 8 | 6.4 | 1.26 (0.54-2.48) | 0.61 |
| | Pol III | all | 837 | 15 | 7.0 | 2.15 (1.21-3.55) | <0.05 |
| | | limited | 135 | 1 | 1.1 | 0.88 (0.02-4.92) | 0.99 |
| | | diffuse | 702 | 14 | 5.8 | 2.40 (1.31-4.03) | <0.01 |
| | CTP-Negative | all | 1,015 | 10 | 7.8 | 1.28 (0.62-2.36) | 0.52 |
| | | limited | 582 | 6 | 4.4 | 1.36 (0.50-2.96) | 0.57 |
| | | diffuse | 433 | 4 | 3.4 | 1.19 (0.32-3.04) | 0.87 |
| After 1st symptom | All | all | 7,157 | 78 | 55.6 | 1.40 (1.11-1.75) | <0.01 |
| | | limited | 3,481 | 31 | 28.1 | 1.10 (0.75-1.57) | 0.63 |
| | | diffuse | 3,676 | 47 | 27.5 | 1.71 (1.25-2.27) | <0.001 |
| | Cenp | all | 1,195 | 8 | 10.7 | 0.75 (0.32-1.48) | 0.52 |
| | | limited | 1,127 | 7 | 10.0 | 0.70 (0.28-1.44) | 0.43 |
| | | diffuse | 68 | 1 | 0.6 | 1.58 (0.04-8.78) | 0.94 |
| | Topo | all | 1,650 | 17 | 13.3 | 1.28 (0.74-2.04) | 0.38 |
| | | limited | 619 | 7 | 5.5 | 1.28 (0.51-2.63) | 0.62 |
| | | diffuse | 1,031 | 10 | 7.9 | 1.27 (0.61-2.34) | 0.53 |
| | Pol III | all | 1,106 | 24 | 9.1 | 2.65 (1.70-3.95) | <0.001 |
| | | limited | 187 | 3 | 1.7 | 1.79 (0.37-5.22) | 0.47 |
| | | diffuse | 919 | 21 | 7.4 | 2.85 (1.76-4.36) | <0.001 |
| | CTP-Negative | all | 1,459 | 16 | 10.4 | 1.53 (0.88-2.49) | 0.13 |
| | | limited | 829 | 10 | 5.8 | 1.71 (0.82-3.15) | 0.15 |
| | | diffuse | 630 | 6 | 4.6 | 1.30 (0.48-2.84) | 0.63 |

*All analyses only include patients with new onset disease (within 5 years of 1st symptom). Non-melanoma skin cancers are excluded.

Breast Cancer

Figure 2:
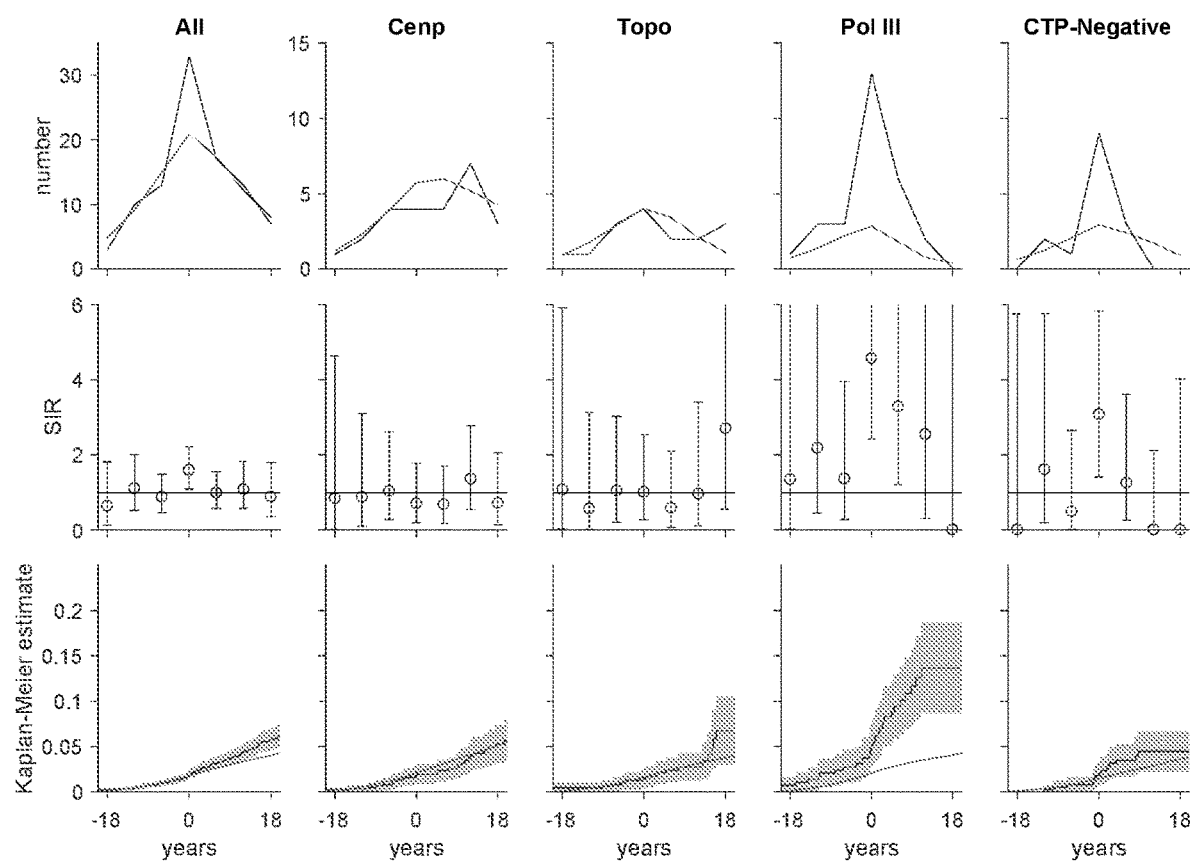
FIG. 2 shows scleroderma patient risk of breast cancers over time. In each graph, the x-axis reflects time from scleroderma onset (defined as time zero); negative time is time before the 1st scleroderma symptom, and positive time is time after the 1st scleroderma symptom. Top row, the observed number of breast cancer cases (blue) is presented in comparison with the number of breast cancer cases that are expected based on SEER data (red). Middle row, the ratio between the observed and expected breast cancer cases is presented as a standardized incidence ratio (SIR) along with its 95% confidence interval. Values of 1 denote a risk of breast cancer equivalent to that of the background population. Each time window represents a 6-year period (i.e. ±3 years) with the graph centered at time 0 (scleroderma onset). Bottom row, the cumulative incidence of breast cancer among scleroderma patients (solid blue line) is presented with 95% confidence intervals (shaded blue region). Red lines represent the expected cumulative incidence of breast cancer based on SEER data for the general population. The overall group with scleroderma (All) and those with topo and cenp antibodies do not have an increased risk of breast cancer. Scleroderma patients with pol III antibodies and the CTP-Negative group have an increased risk of breast cancer that is prominent at scleroderma onset. The cumulative incidence of breast cancer is significantly higher than that observed in the general population among patients with pol III autoantibodies.

Overall, patients with scleroderma did not have an increased risk of breast cancer compared to the general population (SIR 1.03, 95% CI 0.81-1.29; Table 2). However, within 3 years of scleroderma onset, patients with scleroderma have an increased risk of breast cancer (SIR 1.58, 95% CI 1.09-2.22), particularly patients with diffuse disease (SIR 2.19, 95% CI 1.30-3.46). This increased risk of breast cancer-associated scleroderma is likely driven by two subgroups: patients with anti-pol (SIR 4.55, 95% CI 2.42-7.79), particularly those with diffuse disease (SIR 5.64, 95% CI 3.00-9.64), and CTP-negative patients (SIR 3.07, 95% CI 1.40-5.83), particularly those with limited disease (SIR 4.47, 95% CI 1.93-8.81). The marked increased risk of breast cancer at the time of scleroderma onset in these two autoantibody subsets is illustrated in FIG. 2 (top and middle rows). The cumulative incidence of breast cancer is significantly higher among anti-pol patients compared to the general population (bottom row, FIG. 2).

TABLE 3

Risk for breast cancer.

| Analysis time | Antibody | Subtype | Person-years | No. observed | No. expected | SIR (95% CI) | p-value |
|---|---|---|---|---|---|---|---|
| Overall risk | All | all | 36361 | 76 | 73.8 | 1.03 (0.81-1.29) | 0.83 |
| | | limited | 25826 | 47 | 55.1 | 0.85 (0.63-1.14) | 0.31 |
| | | diffuse | 10535 | 29 | 18.8 | 1.54 (1.03-2.22) | <0.05 |
| | Centromere | all | 12261 | 22 | 30.3 | 0.73 (0.46-1.10) | 0.15 |
| | | limited | 11527 | 19 | 28.7 | 0.66 (0.40-1.03) | 0.07 |
| | | diffuse | 734 | 3 | 1.6 | 1.92 (0.40-5.60) | 0.42 |
| | Topo | all | 6844 | 13 | 12.5 | 1.04 (0.56-1.78) | 0.95 |
| | | limited | 3855 | 9 | 7.7 | 1.18 (0.54-2.23) | 0.72 |
| | | diffuse | 2989 | 4 | 4.8 | 0.83 (0.23-2.13) | 0.95 |
| | Pol III | all | 3262 | 20 | 6.5 | 3.08 (1.88-4.76) | <0.001 |
| | | limited | 920 | 2 | 1.8 | 1.12 (0.14-4.06) | 0.99 |
| | | diffuse | 2342 | 18 | 4.7 | 3.82 (2.27-6.04) | <0.001 |
| | CTP-Negative | all | 5487 | 14 | 9.5 | 1.47 (0.80-2.46) | 0.21 |
| | | limited | 3889 | 13 | 6.8 | 1.92 (1.02-3.28) | <0.05 |
| | | diffuse | 1598 | 1 | 2.8 | 0.36 (0.01-2.02) | 0.48 |
| ±3 years | All | all | 13097 | 33 | 20.9 | 1.58 (1.09-2.22) | <0.05 |
| | | limited | 7906 | 15 | 12.7 | 1.18 (0.66-1.95) | 0.59 |
| | | diffuse | 5191 | 18 | 8.2 | 2.19 (1.30-3.46) | <0.01 |
| | Centromere | all | 3206 | 4 | 5.7 | 0.70 (0.19-1.79) | 0.64 |
| | | limited | 2994 | 4 | 5.3 | 0.75 (0.20-1.92) | 0.77 |
| | | diffuse | 212 | 0 | 0.4 | 0.00 (0.00-9.33) | 0.99 |

TABLE 3-continued

Risk for breast cancer.

| Analysis time | Antibody | Subtype | Person-years | No. observed | No. expected | SIR (95% CI) | p-value |
|---|---|---|---|---|---|---|---|
| | Topo | all | 2735 | 4 | 4.0 | 0.99 (0.27-2.54) | 0.99 |
| | | limited | 1344 | 1 | 2.0 | 0.49 (0.01-2.72) | 0.79 |
| | | diffuse | 1391 | 3 | 2.0 | 1.51 (0.31-4.42) | 0.64 |
| | Pol III | all | 1499 | 13 | 2.9 | 4.55 (2.42-7.79) | <0.001 |
| | | limited | 303 | 0 | 0.5 | 0.00 (0.00-6.72) | 0.99 |
| | | diffuse | 1196 | 13 | 2.3 | 5.64 (3.00-9.64) | <0.001 |
| | CTP-Negative | all | 2135 | 9 | 2.9 | 3.07 (1.40-5.83) | <0.01 |
| | | limited | 1330 | 8 | 1.8 | 4.47 (1.93-8.81) | <0.01 |
| | | diffuse | 805 | 1 | 1.1 | 0.88 (0.02-4.88) | 0.99 |

15

Breast Cancer Risk in Patients with Recent Onset Scleroderma

Our findings of an increased risk of breast cancer among all patients with diffuse scleroderma, all anti-pol-positive patients, and anti-pol-positive patients with diffuse scleroderma remained unchanged (Table 4).

TABLE 4

Risk for all breast cancers after 1st visit to Johns Hopkins Scleroderma Center & after 1st scleroderma symptom.*

| Analysis time | Antibody | Subtype | Person-years | No. observed | No. expected | SIR (95% CI) | p-value |
|---|---|---|---|---|---|---|---|
| After 1$^{st}$ visit | All | all | 4900 | 18 | 12.0 | 1.50 (0.89-2.37) | 0.13 |
| | | limited | 2271 | 5 | 6.0 | 0.84 (0.27-1.95) | 0.90 |
| | | diffuse | 2629 | 13 | 6.0 | 2.16 (1.15-3.69) | <0.05 |
| | Cenp | all | 768 | 1 | 2.3 | 0.43 (0.01-2.41) | 0.66 |
| | | limited | 724 | 0 | 2.1 | 0.00 (0.00-1.72) | 0.23 |
| | | diffuse | 44 | 1 | 0.2 | 6.10 (0.15-33.97) | 0.30 |
| | Topo | all | 1169 | 2 | 2.8 | 0.70 (0.09-2.55) | 0.92 |
| | | limited | 403 | 1 | 1.1 | 0.88 (0.02-4.88) | 0.99 |
| | | diffuse | 766 | 1 | 1.7 | 0.59 (0.01-3.28) | 0.99 |
| | Pol III | all | 837 | 9 | 2.2 | 4.15 (1.90-7.87) | <0.001 |
| | | limited | 135 | 1 | 0.4 | 2.85 (0.07-15.87) | 0.59 |
| | | diffuse | 702 | 8 | 1.8 | 4.40 (1.90-8.66) | <0.01 |
| | CTP-Negative | all | 1015 | 3 | 2.3 | 1.33 (0.27-3.88) | 0.79 |
| | | limited | 582 | 3 | 1.4 | 2.18 (0.45-6.37) | 0.32 |
| | | diffuse | 433 | 0 | 0.9 | 0.00 (0.00-4.17) | 0.83 |
| After 1$^{st}$ symptom | All | all | 7157 | 25 | 16.6 | 1.50 (0.97-2.22) | 0.07 |
| | | limited | 3481 | 8 | 8.7 | 0.92 (0.40-1.81) | 0.99 |
| | | diffuse | 3676 | 17 | 7.9 | 2.14 (1.25-3.43) | <0.01 |
| | Cenp | all | 1195 | 1 | 3.4 | 0.29 (0.01-1.63) | 0.29 |
| | | limited | 1127 | 0 | 3.2 | 0.00 (0.00-1.16) | 0.08 |
| | | diffuse | 68 | 1 | 0.2 | 4.20 (0.11-23.41) | 0.42 |
| | Topo | all | 1650 | 3 | 3.8 | 0.79 (0.16-2.30) | 0.95 |
| | | limited | 619 | 1 | 1.7 | 0.60 (0.02-3.34) | 0.99 |
| | | diffuse | 1031 | 2 | 2.1 | 0.94 (0.11-3.38) | 0.99 |
| | Pol III | all | 1106 | 12 | 2.8 | 4.26 (2.20-7.44) | <0.001 |
| | | limited | 187 | 1 | 0.5 | 1.91 (0.05-10.63) | 0.82 |
| | | diffuse | 919 | 11 | 2.3 | 4.80 (2.39-8.58) | <0.001 |
| | CTP-Negative | all | 1459 | 5 | 3.0 | 1.66 (0.54-3.87) | 0.38 |
| | | limited | 829 | 5 | 1.8 | 2.76 (0.90-6.45) | 0.07 |
| | | diffuse | 630 | 0 | 1.2 | 0.00 (0.00-3.05) | 0.60 |

*All analyses only include patients with new onset disease (within 5 years of 1st symptom).

Lung Cancer

Figure 3:
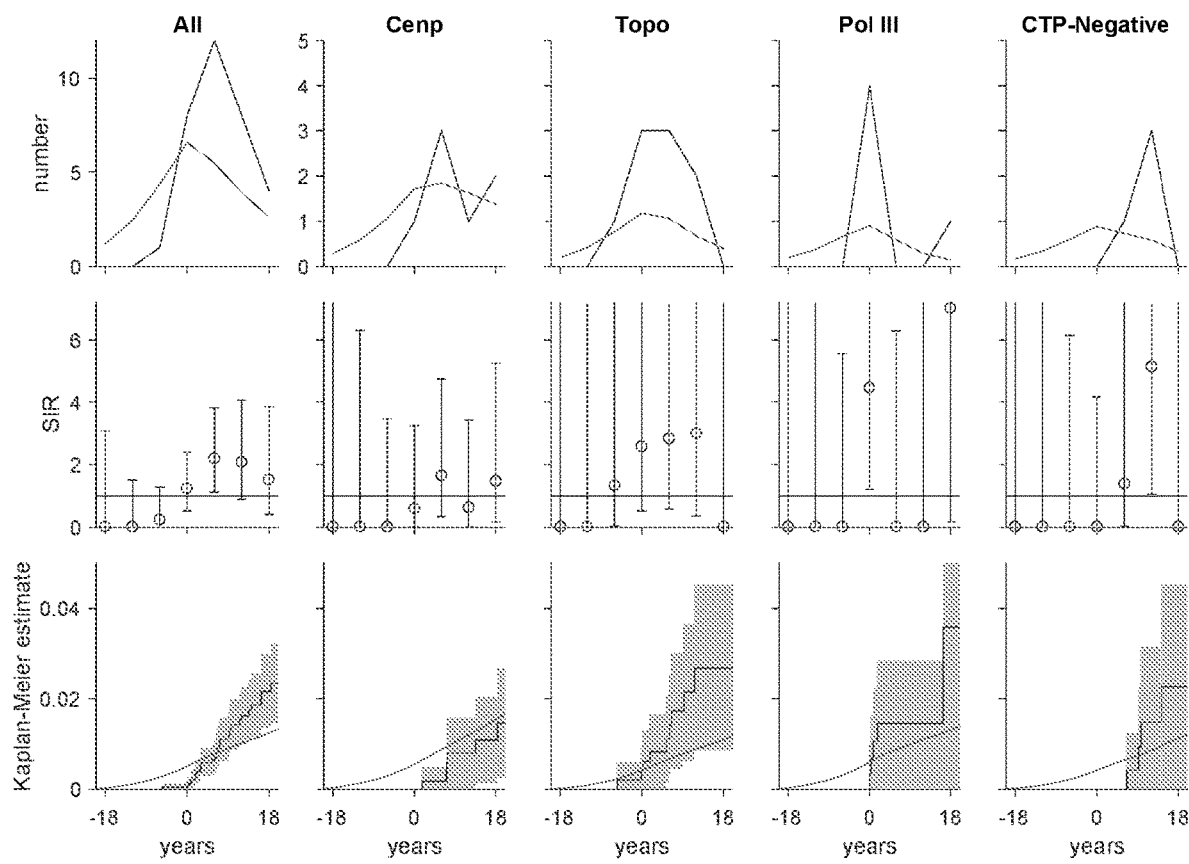
FIG. 3 shows scleroderma patient risk of lung cancers over time. In each graph, the x-axis reflects time from scleroderma onset (defined as time zero); negative time is time before the 1st scleroderma symptom, and positive time is time after the 1st scleroderma symptom. Top row, the observed number of lung cancer cases (blue) is presented in comparison with the number of lung cancer cases that are expected based on SEER data (red). Middle row, the ratio between the observed and expected lung cancer cases is presented as a standardized incidence ratio (SIR) along with its 95% confidence interval. Values of 1 denote a risk of lung cancer equivalent to that of the background population. Each time window represents a 6-year period (i.e. ±3 years) with the graph centered at time 0 (scleroderma onset). Bottom row, the cumulative incidence of lung cancer among scleroderma patients (solid blue line) is presented with 95% confidence intervals (shaded blue region). Red lines in each plot represent the expected cumulative incidence of lung cancer based on SEER data for the general population. Patients with scleroderma (All group) may have an increased risk of lung cancer after scleroderma onset, and this is most notable among patients with topo antibodies. Scleroderma patients with pol III antibodies may also have an increased risk of lung cancer, but in contrast to those with topo antibodies, this risk increase is at the time of scleroderma onset.

Patients with scleroderma had a 65% increased risk of lung cancer compared to the general population (SIR 1.65, 95% CI 1.18-2.25; Table 5). This increased risk was notable in two subsets: those with anti-pol (SIR 2.90, 95% CI 1.06-6.31), with a 6-fold increased risk among the limited cutaneous group (SIR 6.07, 95% CI 1.65-15.6), and those with anti-topo (SIR 2.83, 95% CI 1.41-5.06), especially those with limited disease (SIR 3.49, 95% CI 1.51-6.87). When restricting our analyses to within 3 years of scleroderma onset, an increased risk of lung cancer was seen only in anti-pol patients (SIR 4.45, 95% CI 1.21-11.4) with a markedly increased risk in the limited subset (SIR 10.4, 95% CI 1.26-37.7). In contrast, lung cancers among patients with anti-topo occurred later (FIG. 3).

TABLE 5

Risk for lung cancer.

| Analysis time | Antibody | Subtype | Person-years | No. observed | No. expected | SIR (95% CI) | p-value |
|---|---|---|---|---|---|---|---|
| Overall risk | All | all | 36,361 | 40 | 24.2 | 1.65 (1.18-2.25) | <0.01 |
| | | limited | 25,826 | 31 | 18.1 | 1.72 (1.17-2.44) | <0.01 |
| | | diffuse | 10,535 | 9 | 6.2 | 1.46 (0.67-2.77) | 0.34 |
| | Centromere | all | 12,261 | 10 | 9.8 | 1.02 (0.49-1.87) | 0.99 |
| | | limited | 11,527 | 10 | 9.3 | 1.08 (0.52-1.98) | 0.90 |
| | | diffuse | 734 | 0 | 0.6 | 0.00 (0.00-6.50) | 0.99 |
| | Topo | all | 6,844 | 11 | 3.9 | 2.83 (1.41-5.06) | <0.01 |
| | | limited | 3,855 | 8 | 2.3 | 3.49 (1.51-6.87) | <0.01 |
| | | diffuse | 2,989 | 3 | 1.6 | 1.88 (0.39-5.49) | 0.43 |
| | Pol III | all | 3,262 | 6 | 2.1 | 2.90 (1.06-6.31) | <0.05 |
| | | limited | 920 | 4 | 0.7 | 6.07 (1.65-15.55) | <0.01 |
| | | diffuse | 2,342 | 2 | 1.4 | 1.42 (0.17-5.11) | 0.82 |
| | CTP-Negative | all | 5487 | 4 | 3.2 | 1.25 (0.34-3.21) | 0.79 |
| | | limited | 3889 | 4 | 2.3 | 1.72 (0.47-4.40) | 0.41 |
| | | diffuse | 1598 | 0 | 0.9 | 0.00 (0.00-4.26) | 0.84 |
| ±3 years | All | all | 13,097 | 8 | 6.6 | 1.22 (0.53-2.40) | 0.67 |
| | | limited | 7,906 | 6 | 3.9 | 1.53 (0.56-3.33) | 0.41 |
| | | diffuse | 5,191 | 2 | 2.6 | 0.76 (0.09-2.73) | 0.99 |
| | Centromere | all | 3,206 | 1 | 1.7 | 0.58 (0.01-3.25) | 0.98 |
| | | limited | 2,994 | 1 | 1.6 | 0.62 (0.02-3.46) | 0.99 |
| | | diffuse | 212 | 0 | 0.1 | 0.00 (0.00-35.06) | 0.99 |
| | Topo | all | 2,735 | 3 | 1.2 | 2.56 (0.53-7.48) | 0.23 |
| | | limited | 1,344 | 2 | 0.6 | 3.45 (0.42-12.47) | 0.23 |
| | | diffuse | 1,391 | 1 | 0.6 | 1.69 (0.04-9.40) | 0.89 |
| | Pol III | all | 1,499 | 4 | 0.9 | 4.45 (1.21-11.40) | <0.05 |
| | | limited | 303 | 2 | 0.2 | 10.44 (1.26-37.73) | <0.05 |
| | | diffuse | 1,196 | 2 | 0.7 | 2.83 (0.34-10.22) | 0.32 |
| | CTP-Negative | all | 2135 | 0 | 0.9 | 0.00 (0.00-4.17) | 0.83 |
| | | limited | 1330 | 0 | 0.5 | 0.00 (0.00-6.92) | 0.99 |
| | | diffuse | 805 | 0 | 0.4 | 0.00 (0.00-10.48) | 0.99 |

Lung Cancer Risk in Patients with Recent Onset Scleroderma

In these analyses (Table 6), an increased risk of lung cancer among all patients with scleroderma persists. The findings of an increased risk of lung cancer among anti-pol and anti-topo patients remain in all analyses except for anti-pol patients after first visit to our tertiary referral center.

TABLE 6

Risk for all lung cancers after 1st visit to Johns Hopkins Scleroderma Center & after 1st scleroderma symptom.*

| Analysis time | Antibody | Subtype | Person-years | No. observed | No. expected | SIR (95% CI) | p-value |
|---|---|---|---|---|---|---|---|
| After 1$^{st}$ visit | All | all | 4,900 | 15 | 4.1 | 3.66 (2.05-6.03) | <0.001 |
| | | limited | 2,271 | 9 | 2.0 | 4.44 (2.03-8.43) | <0.001 |
| | | diffuse | 2,629 | 6 | 2.1 | 2.89 (1.06-6.29) | <0.05 |

TABLE 6-continued

Risk for all lung cancers after 1st visit to Johns Hopkins Scleroderma Center & after 1st scleroderma symptom.*

| Analysis time | Antibody | Subtype | Person-years | No. observed | No. expected | SIR (95% CI) | p-value |
|---|---|---|---|---|---|---|---|
| | Cenp | all | 768 | 4 | 0.8 | 4.99 (1.36-12.77) | <0.05 |
| | | limited | 724 | 4 | 0.8 | 5.28 (1.44-13.51) | <0.05 |
| | | diffuse | 44 | 0 | 0.0 | 0.00 (0.00-83.73) | 0.99 |
| | Topo | all | 1,169 | 4 | 1.1 | 3.66 (1.00-9.37) | 0.05 |
| | | limited | 403 | 2 | 0.4 | 4.76 (0.58-17.19) | 0.13 |
| | | diffuse | 766 | 2 | 0.7 | 2.97 (0.36-10.73) | 0.29 |
| | Pol III | all | 837 | 1 | 0.7 | 1.49 (0.04-8.28) | 0.98 |
| | | limited | 135 | 0 | 0.1 | 0.00 (0.00-29.25) | 0.99 |
| | | diffuse | 702 | 1 | 0.5 | 1.83 (0.05-10.19) | 0.84 |
| | CTP-Negative | all | 1015 | 1 | 0.7 | 1.40 (0.04-7.82) | 0.99 |
| | | limited | 582 | 1 | 0.4 | 2.44 (0.06-13.61) | 0.67 |
| | | diffuse | 433 | 0 | 0.3 | 0.00 (0.00-12.16) | 0.99 |
| After 1st symptom | All | all | 7,157 | 18 | 5.6 | 3.22 (1.91-5.09) | <0.001 |
| | | limited | 3,481 | 12 | 2.9 | 4.16 (2.15-7.26) | <0.001 |
| | | diffuse | 3,676 | 6 | 2.7 | 2.22 (0.81-4.83) | 0.11 |
| | Cenp | all | 1,195 | 4 | 1.2 | 3.46 (0.94-8.85) | 0.06 |
| | | limited | 1,127 | 4 | 1.1 | 3.67 (1.00-9.40) | <0.05 |
| | | diffuse | 68 | 0 | 0.1 | 0.00 (0.00-54.40) | 0.99 |
| | Topo | all | 1,650 | 6 | 1.4 | 4.30 (1.58-9.36) | <0.01 |
| | | limited | 619 | 4 | 0.6 | 6.94 (1.89-17.77) | <0.01 |
| | | diffuse | 1,031 | 2 | 0.8 | 2.44 (0.30-8.83) | 0.40 |
| | Pol III | all | 1,106 | 3 | 0.9 | 3.40 (0.70-9.94) | 0.12 |
| | | limited | 187 | 2 | 0.2 | 10.10 (1.22-36.48) | <0.05 |
| | | diffuse | 919 | 1 | 0.7 | 1.46 (0.04-8.15) | 0.99 |
| | CTP-Negative | all | 1459 | 1 | 0.9 | 1.06 (0.03-5.91) | 0.99 |
| | | limited | 829 | 1 | 0.5 | 1.88 (0.05-10.47) | 0.83 |
| | | diffuse | 630 | 0 | 0.4 | 0.00 (0.00-8.97) | 0.99 |

*All analyses only include patients with new onset disease (within 5 years of 1st symptom).

Results of Analyses for Other Cancer Sites (Non-Breast and Non-Lung)

Figure 4:
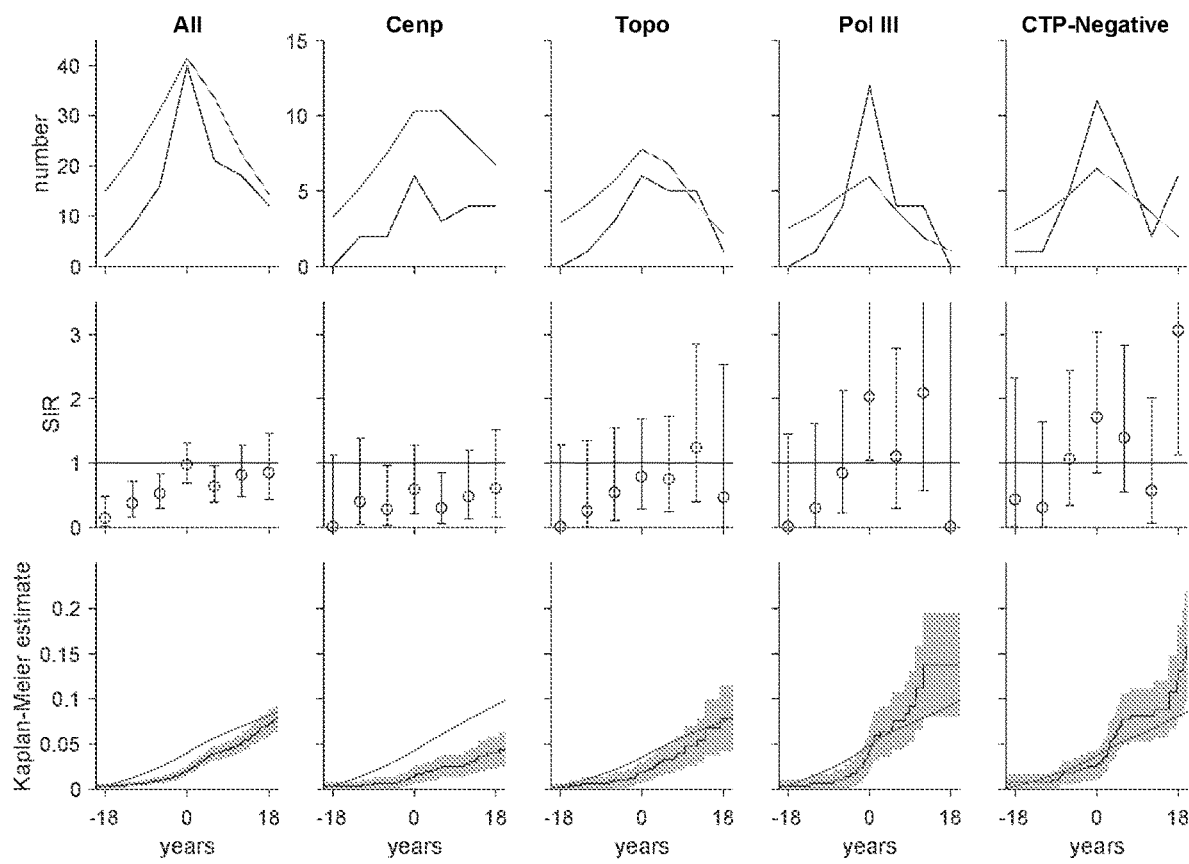
FIG. 4 shows scleroderma patient risk of all cancers, excluding breast, lung and non-melanoma skin, over time. In each graph, the x-axis reflects time from scleroderma onset (defined as time zero); negative time is time before the 1st scleroderma symptom, and positive time is time after the 1st scleroderma symptom. Top row, the observed number of cancer cases (blue) is presented in comparison with the number of cancer cases that are expected based on SEER data (red). Middle row, the ratio between the observed and expected cancer cases is presented as a standardized incidence ratio (SIR) along with its 95% confidence interval. Values of 1 denote a risk of cancer that is equivalent to that of the background population. Each time window represents a 6-year period (i.e. ±3 years) with the graph centered at time 0 (scleroderma onset). Bottom row, the cumulative incidence of cancer among scleroderma patients (solid blue line)

Overall, patients in the cohort had a decreased risk of other cancers (Table 7), and this was most notable in anti-centromere-positive patients (FIG. 4). Patients with anti-pol and diffuse disease had an increased risk, especially within 3 years of scleroderma onset.

Although sample sizes become small, the risk of individual tumor types (melanoma, hematologic, ovary, prostate, tongue, thyroid, and colorectal) within 3 years of scleroderma onset was investigated. Anti-pol patients with diffuse scleroderma had an increased risk of prostate (SIR 7.34, 95% CI 2.00-18.8) and tongue cancer (SIR 46.9, 95% CI 5.68-169.5). Among CTP-negative patients, there was increased melanoma risk in those with limited scleroderma (SIR 7.17, 95% CI 1.48-21.0) and high tongue cancer risk in those with diffuse scleroderma (SIR 42.3, 95% CI 1.07-235.6).

TABLE 7

Risk for all cancers except lung and breast cancer.*

| Analysis time | Antibody | Subtype | Person-years | No. observed | No. expected | SIR (95% CI) | p-value |
|---|---|---|---|---|---|---|---|
| Overall risk | All | all | 36361 | 116 | 139.6 | 0.83 (0.69-1.00) | <0.05 |
| | | limited | 25826 | 67 | 100.3 | 0.67 (0.52-0.85) | <0.001 |
| | | diffuse | 10535 | 49 | 39.3 | 1.25 (0.92-1.65) | 0.15 |
| | Centromere | all | 12261 | 28 | 51.2 | 0.55 (0.36-0.79) | <0.001 |
| | | limited | 11527 | 27 | 48.1 | 0.56 (0.37-0.82) | <0.01 |
| | | diffuse | 734 | 1 | 3.1 | 0.32 (0.01-1.80) | 0.37 |
| | Topo | all | 6844 | 21 | 23.8 | 0.88 (0.55-1.35) | 0.65 |
| | | limited | 3855 | 8 | 13.6 | 0.59 (0.25-146) | 0.15 |
| | | diffuse | 2989 | 13 | 10.3 | 1.27 (0.68-2.17) | 0.47 |
| | Pol III | all | 3262 | 23 | 13.6 | 1.69 (1.07-2.54) | <0.05 |
| | | limited | 920 | 5 | 3.9 | 1.29 (0.42-3.00) | 0.70 |
| | | diffuse | 2342 | 18 | 9.7 | 1.85 (1.10-2.93) | <0.05 |
| | CTP-Negative | all | 5487 | 29 | 20.8 | 1.39 (0.93-2.00) | 0.10 |
| | | limited | 3889 | 20 | 14.7 | 1.36 (0.83-2.09) | 0.22 |
| | | diffuse | 1598 | 9 | 6.1 | 1.48 (0.68-2.82) | 0.32 |
| ±3 years | All | all | 13097 | 40 | 41.6 | 0.96 (0.69-1.31) | 0.89 |
| | | limited | 7906 | 15 | 24.5 | 0.61 (0.34-1.01) | 0.06 |
| | | diffuse | 5191 | 25 | 17.1 | 1.46 (0.95-2.16) | 0.09 |
| | Centromere | all | 3206 | 6 | 10.3 | 0.58 (0.21-1.27) | 0.23 |
| | | limited | 2994 | 6 | 9.7 | 0.62 (0.23-1.35) | 0.30 |
| | | diffuse | 212 | 0 | 0.6 | 0.00 (0.00-6.11) | 0.99 |

TABLE 7-continued

Risk for all cancers except lung and breast cancer.*

| Analysis time | Antibody | Subtype | Person-years | No. observed | No. expected | SIR (95% CI) | p-value |
|---|---|---|---|---|---|---|---|
| | Topo | all | 2735 | 6 | 7.8 | 0.77 (0.28-1.69) | 0.69 |
| | | limited | 1344 | 1 | 3.9 | 0.26 (0.01-1.42) | 0.20 |
| | | diffuse | 1391 | 5 | 3.8 | 1.31 (0.42-3.05) | 0.68 |
| | Pol III | all | 1499 | 12 | 6.0 | 2.02 (1.04-3.52) | <0.05 |
| | | limited | 303 | 1 | 1.1 | 0.89 (0.02-4.96) | 0.99 |
| | | diffuse | 1196 | 11 | 4.8 | 2.28 (1.14-4.08) | <0.05 |
| | CTP-Negative | all | 2135 | 11 | 6.5 | 1.70 (0.85-3.04) | 0.13 |
| | | limited | 1330 | 7 | 3.8 | 1.84 (0.74-3.79) | 0.18 |
| | | diffuse | 805 | 4 | 2.7 | 1.50 (0.41-3.83) | 0.56 |

*Excluding non-melanoma skin cancers.

Together these results demonstrate that an anti-centromere antibody can be used to determine the cancer risk of an SSc patient and/or can be used to prevent and/or treat cancer.

Example 2: Additional Autoantibodies Anti-POLR3-Positive SSc Patients

While the risk of short-interval cancer is increased in SSc patients with RNA polymerase III (POLR3) antibodies, ~80% of anti-POLR3 patients never manifest a cancer.

A novel statistical algorithm was designed to identify new immune responses associated with the absence of cancer in POLR3-positive patients.

Experiments were performed with sera grouped by known antibody status, but differing cancer status, and whether additional specificities are associated with absence of cancer was determined. IPs were performed from radiolabeled HeLa lysates using sera from 10 different anti-POLR3 positive SSc patients. A subgroup of patients with anti-POLR3 but no cancer was identified as also having a novel anti-RNA polymerase I (RPA194) autoantibody (FIG. 5). The anti-RPA194 antibody was not detected in the anti-POLR3-positive cancer group (FIG. 5).

Subsequently, an additional 176 patients with anti-POLR3, 81 of whom (46%) had cancer were also studied. Patients with anti-POLR3 and no cancer were more likely to have anti-RPA194 antibodies than the anti-POLR3 group with cancer (16.8% vs 3.7%, p=0.006), suggesting that the combination of anti-POLR3 and anti-RPA194 may serve as a potent anti-cancer immune response.

These results demonstrate that the combination of an anti-POLR3 antibody and an anti-RPA194 antibody can be used to determine the cancer risk of an SSc patient and/or can be used to prevent and/or treat cancer.

Example 3: Anti-RNPC3 Antibodies as a Marker of Cancer Associated Scleroderma This investigation validated the relationship between anti-RNPC3 antibodies and cancer and examined the associated clinical phenotype in a large sample of scleroderma patients.

Patients and Methods

Study Population and Associated Statistical Analyses

Patients with scleroderma and an available serum sample were identified through the IRB-approved Johns Hopkins Scleroderma Center database. All patients had scleroderma defined by 2013 American College of Rheumatology (ACR) classification criteria, 1980 ACR classification criteria, or having at least 3 of 5 CREST (calcinosis, Raynaud's, esophageal dysmotility, sclerodactyly, telangiectasia) syndrome features (van den Hoogen et al., 2013 Arthritis & Rheum., 65(11):2737-47; and Subcommittee for scleroderma criteria of the American Rheumatism Association Diagnostic and Therapeutic Criteria Committee. 1980 Arthritis & Rheumatism. 23(5):581-90). Demographic data, symptom onset dates, cutaneous subtype (LeRoy et al., 1988 J. Rheumatology, 15(2):202-5), organ-specific severity scores (Clements et al., 1993 J. Rheumatology, 20(11):1892-6; and Medsger et al., 1999 J. Rheumatology, 26(10):2159-67), smoking status, and cancer diagnoses (dates, site, histology and therapy) were captured in all patients at the first visit and longitudinally at 6-month intervals for relevant parameters. All clinically obtained pulmonary function tests and echocardiograms were recorded. The date of scleroderma onset was defined by the date of the first scleroderma symptom, either Raynaud's or non-Raynaud's. The date of cancer diagnosis was obtained from pathology reports or medical record review when available, and was otherwise defined by patient report. The cancer-scleroderma interval was calculated as the difference between these two dates.

Cancer Cohort and Autoantibody Status

The entire cohort of scleroderma patients with cancer was examined and an available serum sample (N=325). The closest serum sample to cancer diagnosis was studied for each participant. Autoantibodies against TOPO, POL, and CENP A/B were assayed by enzyme-linked immunosorbent assays using commercially available kits (Inova Diagnostics), and results ≥40 units were defined as true positives for our primary analyses. A sensitivity analysis was also performed redefining antibody positivity as ≥20 units. Autoantibodies to RNPC3 were assayed by immunoprecipitation of 35S-methionine labeled protein generated by in vitro transcription and translation from cDNA encoding full length RNPC3 (purchased from Origene Technologies) as described elsewhere (Fiorentino et al., 2013 Arthritis & Rheum., 65(11):2954-62). Representative data from the immunoprecipitation assay to detect RNPC3 antibodies is shown in FIG. 6. Primary analyses were restricted to patients who were positive for only 1 scleroderma autoantibody, as previously described (Shah et al., 2015 Arthritis & Rheumatology, 67(4):1053-61). Of 325 patients with complete autoantibody data, only 7 patients were excluded from our analyses due to positivity for multiple autoantibodies, largely due to overlap with anti-centromere antibodies. Five of the 7 also had anti-RNPC3 antibodies, only 3 of whom were moderately or strongly positive. Therefore, the study population consisted of 318 scleroderma patients with cancer.

Patients were subdivided into 5 autoantibody categories for analysis: anti-POL, anti-TOPO, anti-CENP, anti-RNPC3, and "CENP/TOPO/POL/RNPC3 (CTPR)-negative" (i.e. those who were negative for the 4 tested autoantibodies). Demographics, cancer-scleroderma interval, and scleroderma phenotypic features were compared across autoantibody subgroups. For continuous variables, differences in means were assessed by analysis of variance (ANOVA) unless unequal variances were suggested by Bartlett's test; in this instance, the Kruskal-Wallis test was applied as a nonparametric test. Dichotomous and categorical variables were compared using the Fisher's exact test. Characteristics were also compared between anti-RNPC3 positive vs. negative patients using the Student's t test and Fisher's exact test where appropriate.

Logistic regression analysis was performed to examine whether anti-RNPC3 and other autoantibodies associate with an increased risk of cancer-associated scleroderma. Cancer-associated scleroderma was defined by a short cancer-scleroderma interval (±2 years), as previously elsewhere (Shah et al., 2015 *Arthritis & Rheumatology*, 67(4):1053-61). The cancer-scleroderma interval was also examined graphically by generating scatterplots of age at scleroderma onset and age at cancer diagnosis for each autoantibody type.

Comparison with CTP-Negative Scleroderma Patients without Cancer

Sixty CTP-negative scleroderma patients without cancer were also studied. The prevalence of anti-RNPC3 positivity was compared between CTP-negative patients with cancer and without cancer by the chi-square test. Whether the clinical phenotype differed between anti-RNPC3 positive patients with and without cancer was examined using the Wilcoxon-Mann-Whitney test and Fisher's exact test where appropriate.

Comparison with Healthy Controls and Other Disease States

Twenty-five healthy controls, 45 patients with pancreatic cancer, and 35 patients with lupus and cancer were also assayed for anti-RNPC3 as described above.

All statistical analyses were performed using Stata version 13 (StataCorp, College Station, Tex.). Two sided p-values <0.05 were considered statistically significant. Odds ratios (ORs) with 95% confidence intervals (95% CIs) are provided.

Results

Three hundred eighteen scleroderma patients with cancer were analyzed (Table 8). Seventy patients (22.0%) were positive for anti-POL antibodies, 54 (17.0%) for anti-TOPO, 96 (30.2%) for anti-CENP, and 12 (3.8%) for anti-RNPC3, leaving 86 (27.0%) patients who likely target other specificities (the CTPR-negative group). None of the controls (healthy, pancreatic cancer, or lupus and cancer) had evidence of anti-RNPC3 antibodies.

TABLE 8

Characteristics of study population (N = 318 patients with SSc and cancer).

| Variable | POL (N = 70) | TOPO (N = 54) | CENP (N = 96) | RNPC3 (N = 12) | CTPR-Negative (N = 86) | P-Value |
|---|---|---|---|---|---|---|
| Age SSc onset (years), mean (SD) | 52.7 (13.0) | 43.8 (16.3) | 43.8 (14.7) | 50.1 (11.7) | 47.9 (13.7) | 0.0007 |
| Age at cancer diagnosis (years), mean (SD) | 56.3 (10.8) | 52.2 (14.8) | 56.3 (13.4) | 48.6 (13.2) | 56.3 (12.8) | 0.1059 |
| SSc-cancer interval (years), median (IQR) | 1.0 (−1.3, 8.9) | 7.7 (0.3, 14.1) | 11.1 (1.3, 25.8) | 0.9 (−5.0, 2.7) | 7.5 (1.4, 16.7) | 0.0001^ |
| nonRP-cancer interval (years), median (IQR) | 0.8 (−2.0, 5.5), N = 69 | 6.0 (−1.4, 13.0), N = 52 | 5.3 (−1.5, 13.8), N = 95 | −0.1 (−8.5, 0.5) | 3.7 (−1.2, 12.0), N = 85 | 0.0021^ |
| RP-cancer interval (years), median (IQR) | 0.8 (−1.7, 8.5), N = 68 | 7.7 (0.3, 14.1) | 9.2 (−0.1, 24.6) | 0.9 (−5.0, 2.7) | 8.7 (0.8, 16.4), N = 78 | 0.0008^ |
| Disease duration at 1st visit, median (IQR) | 1.6 (1.0, 4.2) | 3.6 (1.5, 12.2) | 13.5 (5.1, 26.2) | 2.2 (1.1, 6.6) | 6.1 (1.0, 12.4) | 0.0001^ |
| Female sex, no. (%) | 52 (74.3) | 43 (79.6) | 86 (89.6) N = 95 | 12 (100) | 66 (76.7) N = 85 | 0.024 |
| Race, no. (%) | | | | | | 0.001 |
| White | 69 (98.6) | 46 (85.2) | 93 (97.9) | 9 (75) | 75 (88.2) | |
| Black | 1 (1.4) | 5 (9.3) | 2 (2.1) | 3 (25) | 8 (9.4) | |
| Other | 0 (0) | 3 (5.6) | 0 (0) | 0 (0) | 2 (2.4) | |
| Smoking, no. (%) | | | N = 95 | | | 0.912 |
| Never | 33 (47.2) | 27 (50) | 48 (50.5) | 7 (58.3) | 35 (40.7) | |
| Former | 29 (41.4) | 22 (40.7) | 37 (39) | 4 (33.3) | 43 (50) | |
| Current | 8 (11.4) | 5 (9.3) | 10 (10.5) | 1 (8.3) | 8 (9.3) | |
| 2013 ACR classification criteria*, no. (%) | 92 (95.8) | 70 (100) | 54 (100) | 12 (100) | 82 (95.4) | 0.201 |
| Cutaneous subtype, no. (%) | | | | | | |
| Diffuse | 54 (77.1) | 23 (42.6) | 6 (6.3) | 3 (25) | 29 (33.7) | <0.001 |
| Limited | 16 (22.9) | 31 (57.4) | 90 (93.8) | 9 (75) | 57 (66.3) | |
| Baseline mRSS, median (IQR) | 18 (8, 30), N = 69 | 6 (3, 15), N = 51 | 2 (2, 4), N = 91 | 2 (2, 4) | 4 (2, 13), N = 77 | 0.0001^ |
| Baseline Medsger disease severity scores**, no. (%) Severe RP (pits, ulcers, gangrene) | 9 (12.9) | 25 (46.3) | 32 (33.3) | 7 (58.3) | 21 (25), N = 84 | <0.001 |

TABLE 8-continued

Characteristics of study population (N = 318 patients with SSc and cancer).

| Variable | POL (N = 70) | TOPO (N = 54) | CENP (N = 96) | RNPC3 (N = 12) | CTPR-Negative (N = 86) | P-Value |
|---|---|---|---|---|---|---|
| Severe GI disease (≥2) | 5 (7.1) | 12 (22.2) | 21 (21.9) | 3 (25) | 26 (30.6), N = 85 | 0.005 |
| Severe lung disease (FVC or DLCO < 70% pred) | 17 (34), N = 50 | 23 (57.5), N = 40 | 29 (44.6), N = 65 | 8 (88.9), N = 9 | 31 (49.2), N = 63 | 0.019 |
| Baseline FVC (% predicted), mean (SD) | 84.6 (14.3), N = 62 | 73.2 (16.9), N = 49 | 90.0 (16.1), N = 91 | 66.1 (17.8) | 77.7 (19.5), N = 78 | <0.0001 |
| Baseline DLCO (% predicted), mean (SD) | 83.6 (20.2), N = 55 | 74.7 (22.4), N = 46 | 85.2 (25.1), N = 79 | 64.2 (23.4), N = 8 | 71.4 (22.1), N = 70 | 0.0005 |
| Baseline RVSP (mmHg), median (IQR) | 33.2 (26, 38), N = 38 | 31 (27.5, 35.5), N = 32 | 35 (28, 43), N = 53 | 43 (35, 51), N = 6 | 34 (30, 42), N = 57 | 0.0206^ |
| FVC ever < 70% predicted, no. (%) | 22 (31.4) | 34 (63) | 26 (27.1) | 9 (75) | 36 (41.9) | <0.001 |
| RVSP ever > 45 mmHg, no. (%) | 14 (20) | 16 (29.6) | 34 (35.4) | 6 (50) | 33 (38.4) | 0.062 |
| Myopathy ever, no.(%)*** | 10 (14.3) | 5 (9.3) | 6 (6.3) | 4 (33.3) | 15 (17.4) | 0.027 |
| Tendon friction rubs ever, no. (%) | 32 (45.7) | 12 (22.2) | 3 (3.1) | 0 (0) | 8 (9.3) | <0.001 |
| Renal crisis, no. (%) | 9 (12.9) | 1 (1.9) | 1 (1.0) | 1 (8.3) | 6 (7.0) | 0.009 |
| Death | 25 (35.7) | 21 (38.9) | 26 (27.1) | 7 (58.3) | 35 (40.7) | 0.134 |
| Cancer site, no. (%) Female/gynecologic | | | | | | NT |
| Breast | 27 (38.6) | 17 (31.5) | 29 (30.2) | 6 (50) | 18 (20.9) | |
| Other gynecologic | 5 (7.1) | 3 (5.6) | 9 (9.4) | 2 (16.7) | 7 (8.1) | |
| Lung | 6 (8.6) | 9 (16.7) | 11 (11.5) | 0 (0) | 6 (7) | |
| Hematologic | 3 (4.3) | 0 (0) | 8 (8.3) | 2 (16.7) | 11 (12.8) | |
| Skin | 8 (11.4) | 12 (22.2) | 24 (25) | 2 (16.7) | 25 (29.1) | |
| Others | 21 (30) | 13 (24.1) | 15 (15.6) | 0 (0) | 19 (22.1) | |

*The 4 remaining patients in the anti-CENP group and 3 of the 4 in the CTPR-negative group met at least 3 of 5 CREST criteria; one patient in the CTPR-negative group met 1980 ACR classification criteria.
**Severe Raynaud's defined by a Medsger severity score at baseline ≥2 (pits, ulcers, gangrene); severe lung severity score defined by FVC or DLCO <70% predicted; severe GI severity score defined by requirement of high dose medications for gastroesophageal reflux disease, antibiotics needed for bacterial overgrowth, malabsorption syndrome, episodes of pseudo-obstruction, or requirement of total parenteral nutrition.
***Myopathy defined by a history of abnormal muscle enzymes or abnormal findings on electromyography, muscle biopsy or magnetic resonance imaging.
^denote analyses performed using the Kruskal-Wallis test; medians and interquartile ranges (IQR) are presented. Abbreviations: POL = RNA polymerase III; Topo = Topoisomerase 1; Cenp = Centromere; CTPR-Negative = Negative for centromere, topoisomerase 1, RNA polymerase III and RNPC3; SSc = systemic sclerosis; RP = Raynaud's phenomenon; ACR = American College of Rheumatology; mRSS = modified Rodnan skin score; GI = gastrointestinal; FVC = forced vital capacity; DLCO = diffusing capacity; RVSP = right entricular ystolic pressure; NT = Not tested

RNPC3 Autoantibodies Associate with a Short Cancer-Scleroderma Interval and Severe Clinical Phenotype The cancer-scleroderma interval was significantly different across the 5 autoantibody subgroups; this finding persisted whether scleroderma onset was defined by Raynaud's onset (p=0.0008), the first non-Raynaud's symptom (p=0.0021), or the first symptom (either Raynaud's or non-Raynaud's; p=0.0001). Patients with anti-RNPC3 autoantibodies had a short cancer-scleroderma interval (median 0.9 years), similar to that observed for patients with anti-POL antibodies (median 1.0 years). This temporal clustering between cancer and scleroderma for anti-RNPC3 and anti-POL positive patients is illustrated in FIG. 7. The line in each scatterplot represents where the age of cancer diagnosis equals the age at scleroderma onset (i.e., cancer-scleroderma interval=0). Patients with anti-RNPC3 autoantibodies clustered tightly on or around the line of perfect agreement, consistent with cancer-associated scleroderma. Relative to patients with anti-CENP autoantibodies, patients with anti-RNPC3 antibodies (OR 4.3; 95% CI 1.10, 16.9; p=0.037) and anti-POL antibodies (OR 4.49; 95% CI 1.98, 10.2; p<0.001) had a >4 fold increased risk of cancer within 2 years of scleroderma onset (Table 9). When broadening our reference group to include patients with anti-CENP, anti-TOPO and those who are CTPR-Negative, patients with anti-RNPC3 (OR 3.57; 95% CI 1.01, 12.6; p=0.048) and anti-POL (OR 3.72; 95% 1.99, 6.98; p<0.001) had a >3 fold increased odds of cancer within 2 years of scleroderma onset. These findings persisted in the sensitivity analyses that redefined autoantibody positivity with a lower cutoff of ≥20 units.

TABLE 9

Relative odds (95% CI) of cancer-associated scleroderma.*

| Autoantibody | Cancer-associated scleroderma |
|---|---|
| Centromere (CENP) | Reference |
| RNA polymerase III (POL) | 4.49 (1.98, 10.2) |
| Topoisomerase 1 (TOPO) | 1.72 (0.65, 4.54) |
| RNPC3 | 4.3 (1.10, 16.9) |
| Remaining (CTPR-Negative) | 1.13 (0.45, 2.87) |

*Cancer-associated scleroderma defined as cancer and scleroderma occurring within 2 years of each other (±2 years)

Patients with anti-RNPC3 autoantibodies were 100% female and more likely to be black (25%) (Table 8). There were statistically significant differences in age at scleroderma onset (p=0.0007) and disease duration at first visit (p=0.0001) across autoantibody categories. Patients with anti-RNPC3 and anti-POL antibodies had a mean age of scleroderma onset above 50 years and a shorter time to presentation for clinical evaluation than the other antibody subgroups, likely due to the aggressive phenotype associated with these two autoantibodies (Nikpour et al., 2011 *Arthritis Research & Therapy*, 13(6):R211; and Fertig et al., 2009 *Arthritis & Rheum.*, 61(7):958-65). While patients with anti-RNPC3 antibodies had less severe cutaneous and articular disease as assessed by subtype, modified Rodnan skin scores, and the presence of tendon friction rubs, they had more severe restrictive lung disease at baseline with lower forced vital capacity and diffusing capacity and higher Medsger lung severity scores. Anti-RNPC3 positive patients also had associated pulmonary hypertension as defined by elevated right ventricular systolic pressure (RVSP) on baseline echocardiography, although it is important to note the small sample size of patients with an estimated RVSP for this analysis. Anti-RNPC3 patients had an associated myopathy (33.3%), severe gastrointestinal disease and severe Raynaud's phenomenon.

Given the sample size, pairwise comparisons between the anti-RNPC3 autoantibody group with every other autoantibody group were not performed because of the high likelihood that associations would be observed by chance alone. However, anti-RNPC3-positive and -negative patients were compared and it was confirmed that anti-RNPC3 positive patients had statistically significant associations with a short cancer-scleroderma interval, severe restrictive lung disease consistent with ILD, a higher baseline RVSP, severe Raynaud's phenomenon, and history of myopathy.

While anti-RNPC3 autoantibodies were not commercially available for clinical use, indirect immunofluorescence patterns on ANA testing may provide insight into CTP-negative patients who could have this specificity. Of the 12 anti-RNPC3 positive patients, 11 had available data on ANA pattern. Nine of the 11 patients (81.8%) had a speckled pattern. As some of the phenotypic features that associate with anti-RNPC3 autoantibodies were similar to that seen in patients with anti-U1RNP, whether anti-U1RNP is also present among these patients was assessed by ELISA. No patient with anti-RNPC3 autoantibodies was moderately to strongly positive for anti-U1RNP.

Patients with anti-RNPC3 antibodies also had a worse prognosis with a shorter time to death compared to patients in the other autoantibody subgroups (FIG. 8; median survival 9.0 years in anti-RNPC3 vs. >20 years in all other antibody groups; log rank test p<0.0001). While statistical comparisons of all tumor types were not possible with the sample size, it is noteworthy that most malignancies (66.7%) in the anti-RNPC3 group were female/gynecologic tumors, with 50% being breast cancers (p=0.075 for comparison across antibody groups).

Prevalence of Anti-RNPC3 Autoantibodies and Clinical Phenotype of Anti-RNPC3 Positive Patients does not Differ by Cancer Status Among CTP-negative scleroderma patients, there were no significant differences in the prevalence of anti-RNPC3 antibodies by cancer status ($12/98$ (12.2%) with cancer were anti-RNPC3 positive, compared to $8/60$ (13.3%) of those without cancer; p=0.842). Whether unique phenotypic features could identify the subset of patients with an underlying cancer among anti-RNPC3 positive patients was examined, as clinical differences could aid in risk stratification for cancer screening. The sample size was limited to 12 anti-RNPC3 positive patients with cancer and 8 anti-RNPC3 positive patients without cancer. There were no statistical differences in age at scleroderma onset, age at cancer diagnosis, disease duration at first visit, gender, race, cutaneous subtype, organ specific severity scores, baseline pulmonary function, myopathy or articular disease.

These results demonstrate that an anti-RNPC3 antibody can be used to determine the cancer risk of an SSc patient and/or can be used to prevent and/or treat cancer.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating cancer in a subject having an autoimmune disease comprising:
   identifying the subject as having cancer cells; and
   administering to the subject:
   (i) an anti-RNA polymerase III antibody or antibody fragment, and
   (ii) an anti-RPA194 antibody or antibody fragment;
   wherein the number of cancer cells within the subject is reduced; and
   wherein the autoimmune disease is selected from the group consisting of: scleroderma, systemic lupus erythematosus, and myositis.

2. The method of claim 1, wherein the cancer is selected from the group consisting of: breast cancer, lung cancer, head and neck cancer, tongue cancer, prostate cancer, and melanoma.

3. The method of claim 1, wherein the subject is a human.

4. The method of claim 1, wherein the antibody or antibody fragment is chimeric, humanized, or fully human.

* * * * *

UNITED STATES PATENT AND TRADEMARK OFFICE
CERTIFICATE OF CORRECTION

| | |
|---|---|
| PATENT NO. | : 11,454,630 B2 |
| APPLICATION NO. | : 16/640954 |
| DATED | : September 27, 2022 |
| INVENTOR(S) | : Ami A. Shah et al. |

It is certified that error appears in the above-identified patent and that said Letters Patent is hereby corrected as shown below:

In the Claims

Claim 1: Column 34, Line 33, delete "Ill" and insert -- III --.

Signed and Sealed this
Fourth Day of April, 2023

Katherine Kelly Vidal
*Director of the United States Patent and Trademark Office*